United States Patent [19]

Green et al.

[11] Patent Number: 5,431,322
[45] Date of Patent: Jul. 11, 1995

[54] SELF CONTAINED GAS POWERED SURGICAL APPARATUS

[75] Inventors: David T. Green, Westport; Henry Bolanos, East Norwalk; Keith Ratcliff, Sandy Hook; Jeffrey J. Blewett, Plantsville; Randolph F. Lehn, Bridgeport; Charles R. Sherts, Southport; Graham W. Bryan, Norwalk; Salvatore Castro, Waterbury; Gary S. Kappel, Stamford, all of Conn.

[73] Assignee: United States Surgical Corporation, Norwalk, Conn.

[21] Appl. No.: 146,804

[22] Filed: Nov. 2, 1993

Related U.S. Application Data

[63] Continuation of Ser. No. 915,425, Jul. 17, 1992, abandoned, which is a continuation of Ser. No. 781,012, Oct. 18, 1991, abandoned.

[51] Int. Cl.$^6$ .......................................... A61B 17/068
[52] U.S. Cl. .................... 227/176; 227/179; 227/180; 227/19; 227/8
[58] Field of Search ............... 227/175, 176, 178, 179, 227/180, 182, 19, 8

[56] References Cited

U.S. PATENT DOCUMENTS

| | | |
|---|---|---|
| Re. 28,932 | 8/1976 | Noiles et al. |
| 2,448,741 | 9/1948 | Scott et al. |
| 3,717,294 | 2/1973 | Green ................... 227/19 |
| 3,735,762 | 5/1973 | Bryan et al. ............ 227/19 |
| 3,819,100 | 6/1974 | Noiles et al. |
| 3,837,555 | 9/1974 | Green ................... 227/19 |
| 3,949,924 | 4/1976 | Green. |
| 4,169,476 | 10/1979 | Hiltebrandt. |
| 4,273,129 | 6/1981 | Boebel. |
| 4,331,277 | 5/1982 | Green ................... 227/19 |
| 4,383,634 | 5/1983 | Green. |
| 4,520,817 | 6/1985 | Green. |
| 4,540,110 | 9/1985 | Bent et al. ............. 227/19 |
| 4,566,620 | 1/1986 | Green et al. |
| 4,573,468 | 3/1986 | Conta et al. |
| 4,573,622 | 3/1986 | Green et al. |
| 4,580,712 | 4/1986 | Green. |
| 4,610,383 | 9/1986 | Rothfuss et al. ........ 227/19 |
| 4,633,874 | 1/1987 | Chow et al. |
| 4,714,187 | 12/1987 | Green. |
| 4,715,520 | 12/1987 | Roehr, Jr. et al. |
| 4,728,020 | 3/1988 | Green et al. |
| 4,819,853 | 4/1989 | Green. |
| 4,848,637 | 7/1989 | Pruitt. |
| 4,938,408 | 7/1990 | Bedi et al. ............. 227/19 |
| 4,941,623 | 7/1990 | Pruitt. |
| 4,955,959 | 9/1990 | Tompkins et al. |
| 4,978,049 | 12/1990 | Green. |
| 5,018,657 | 5/1991 | Pedlick et al. ......... 227/19 |
| 5,040,715 | 8/1991 | Green et al. ........... 227/8 |
| 5,047,038 | 9/1991 | Peters et al. |
| 5,170,925 | 12/1992 | Madden et al. ......... 227/19 |

FOREIGN PATENT DOCUMENTS

| | | |
|---|---|---|
| 0041022 | 12/1981 | European Pat. Off. |
| 0156774 | 2/1985 | European Pat. Off. |
| 0324166 | 7/1989 | European Pat. Off. |
| 0324637 | 7/1989 | European Pat. Off. |
| 0365153 | 4/1990 | European Pat. Off. |
| 0373762 | 6/1990 | European Pat. Off. |
| 0399701 | 11/1990 | European Pat. Off. |
| 51-149985 | 5/1975 | Japan. |
| 728848 | 5/1980 | U.S.S.R. |

Primary Examiner—Scott A. Smith

[57] ABSTRACT

A self contained gas powered endoscopic surgical apparatus is provided for placing lateral lines of surgical fasteners into body tissue. The apparatus includes an anvil member and a surgical fastener cartridge member mounted to the distal end of an elongated endoscopic portion. A tubular collar of the endoscopic portion moves distally to engage the anvil member and bias the anvil member and the cartridge member into cooperative alignment, thereby clamping body tissue to be fastened between the anvil member and the cartridge member. A self contained pneumatic system is disposed in the surgical apparatus and is actuable to eject and/or form the surgical fasteners in the clamped body tissue. The apparatus further comprises a locking mechanism for preventing firing of the instrument after it has been fired a predetermined number of times. A counter for displaying the number of times the apparatus has been fired may be provided. A firing interlock is also shown which prevents accidental actuation of the firing trigger. A clamping interlock is shown which prevents approximation of the jaws when the jaws are either misaligned or improperly inserted into the instrument.

39 Claims, 25 Drawing Sheets

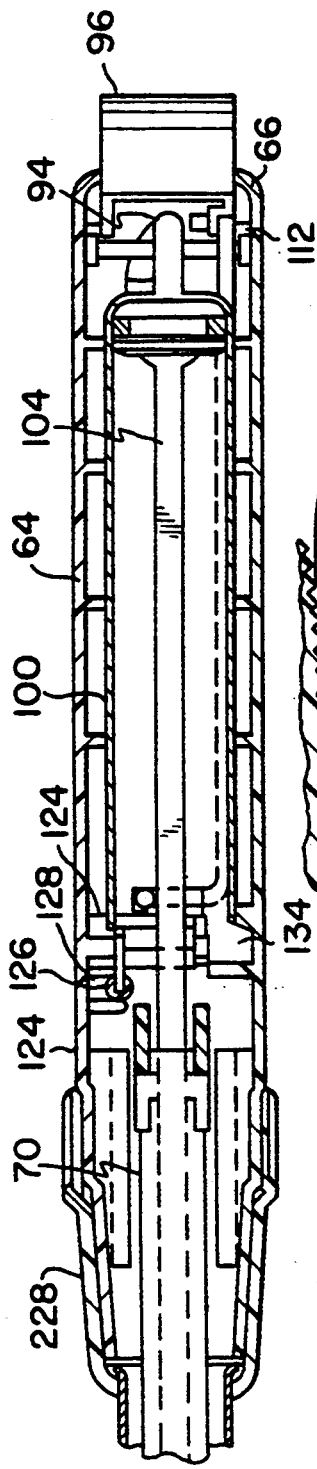
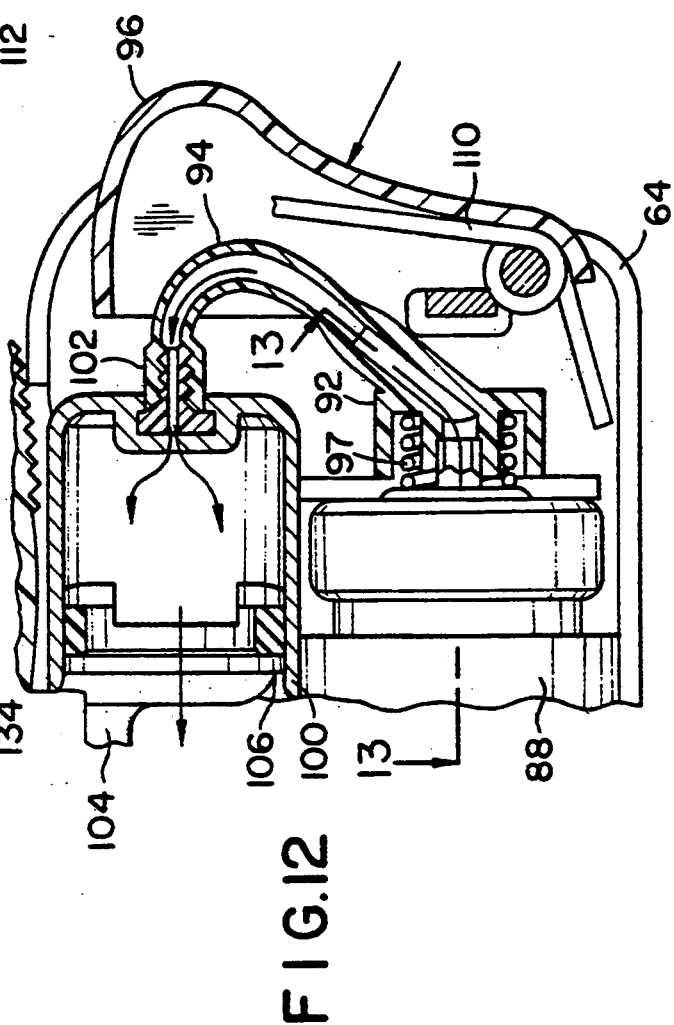

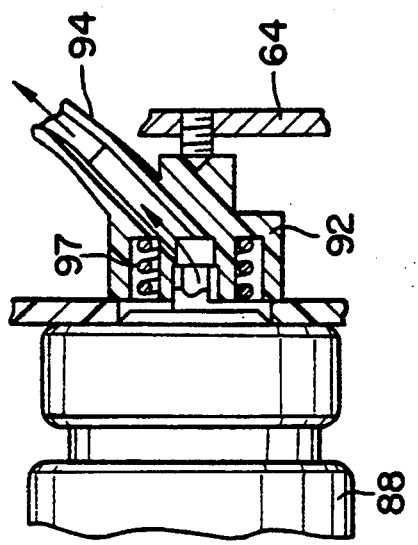
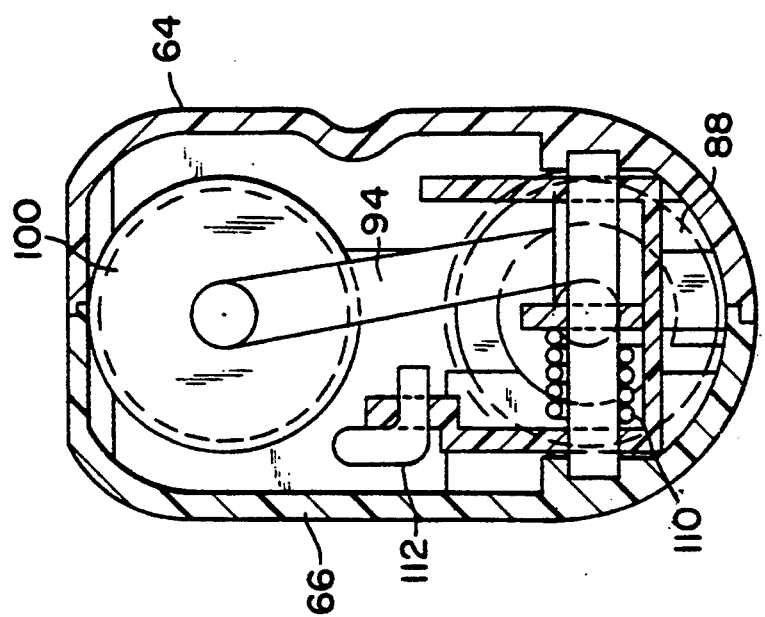

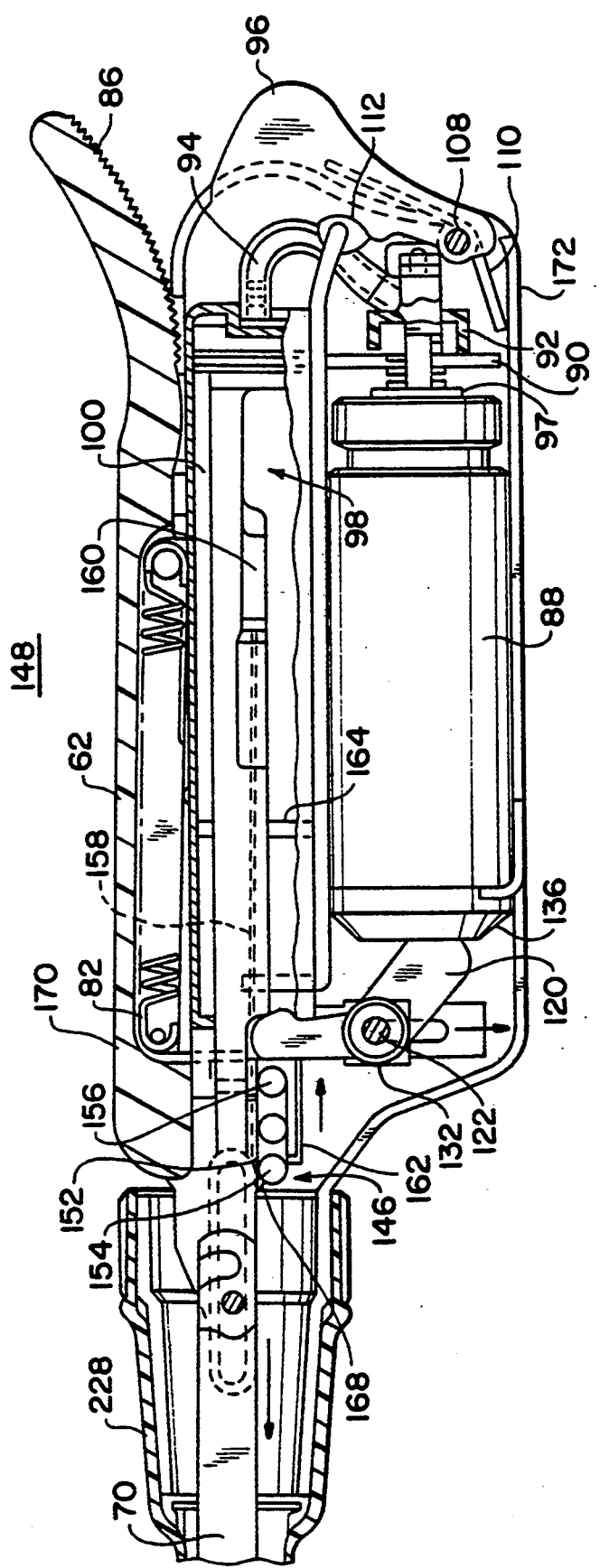

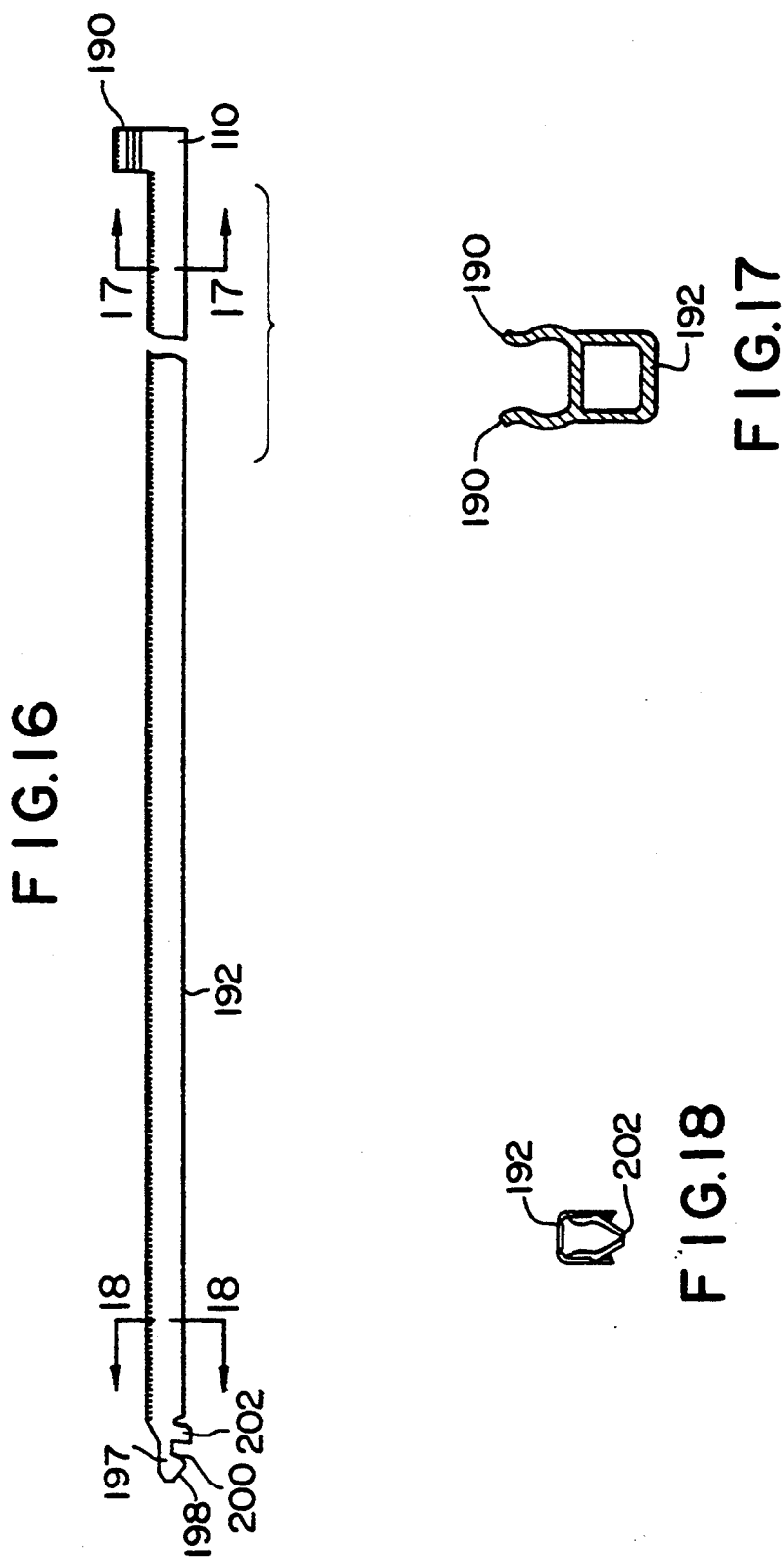

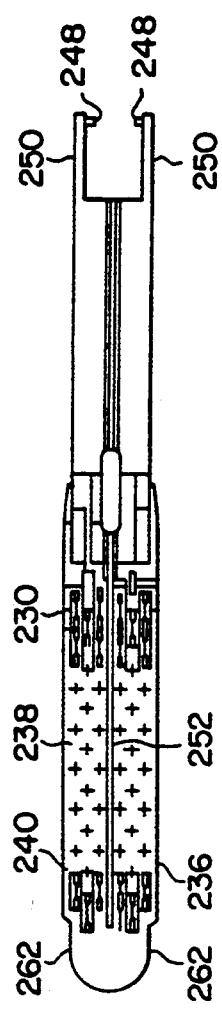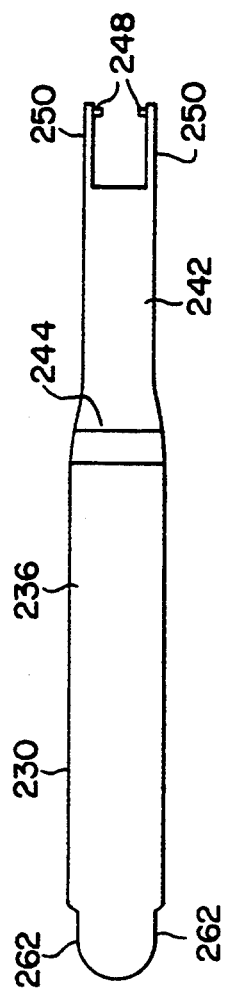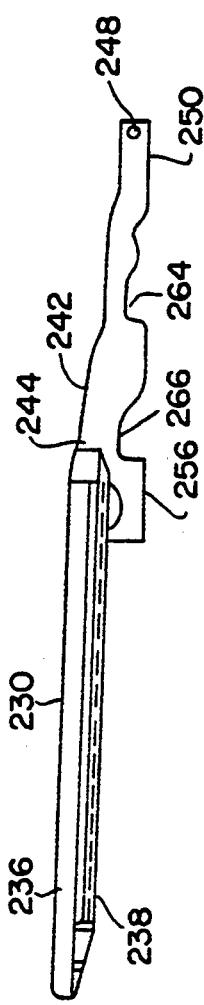

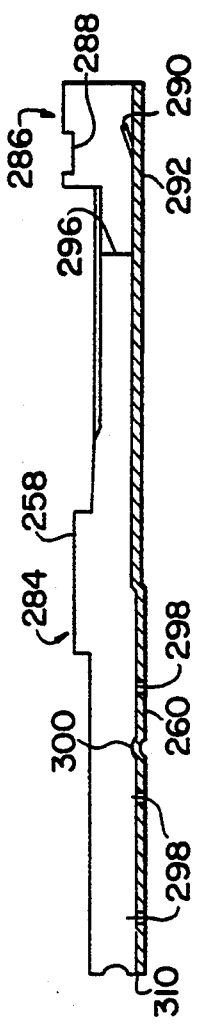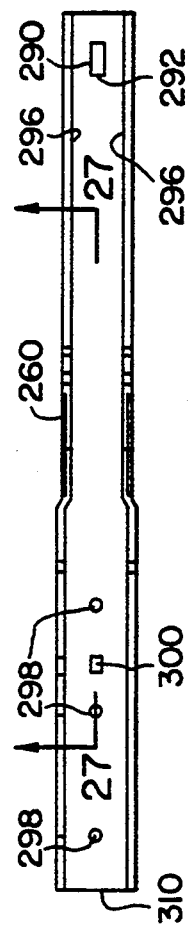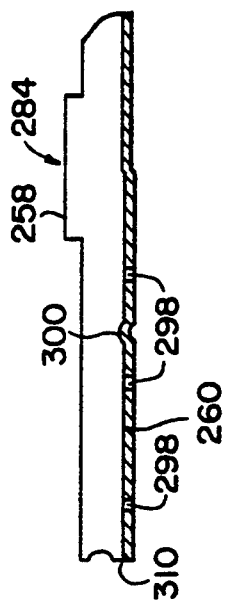

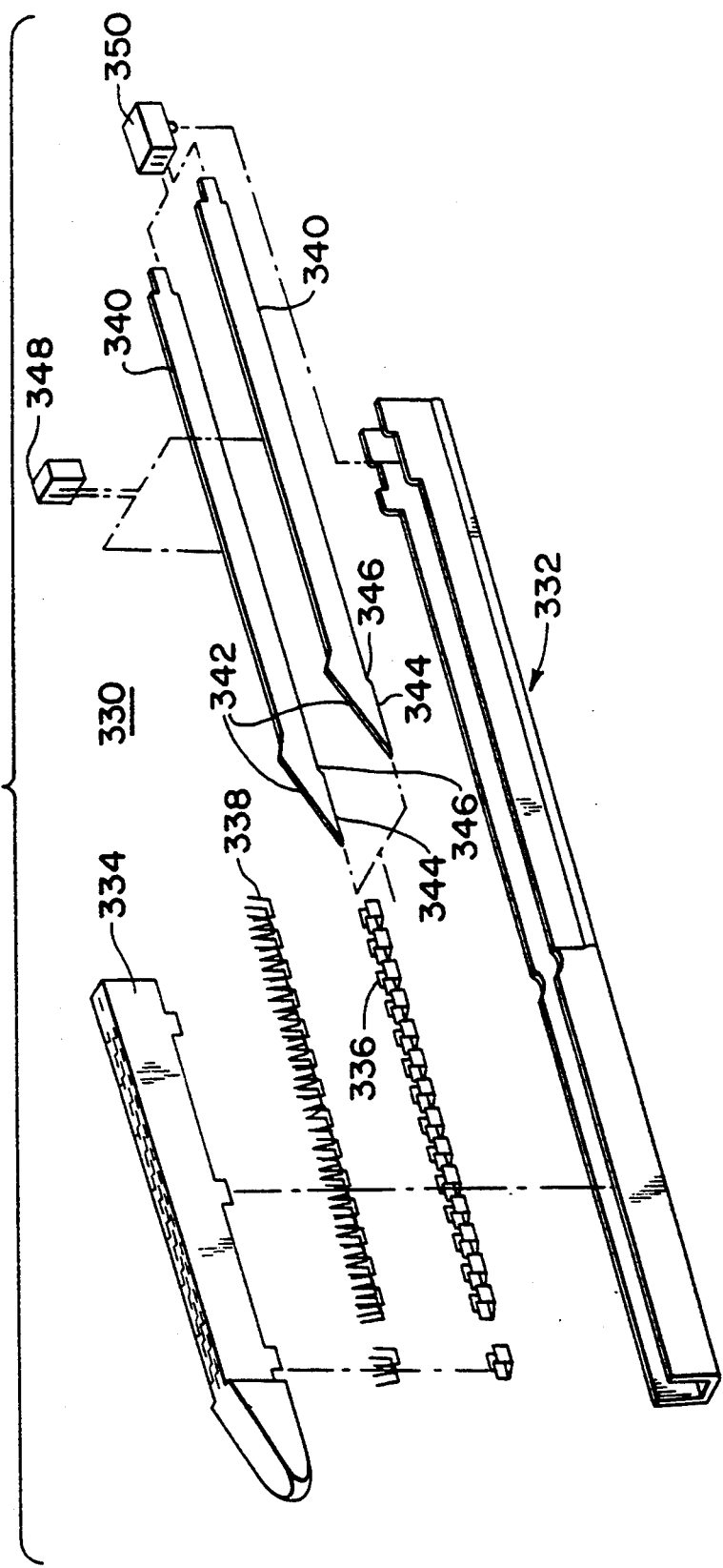

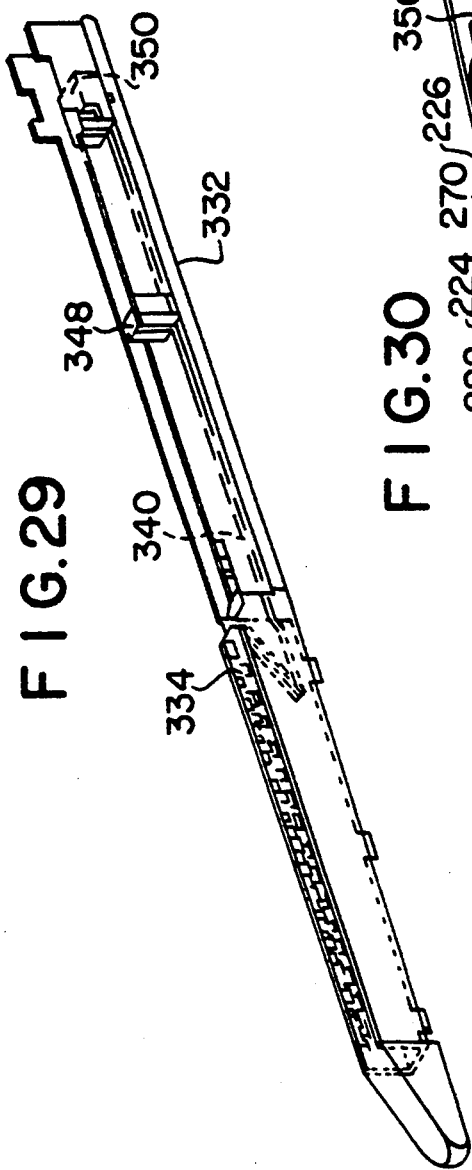
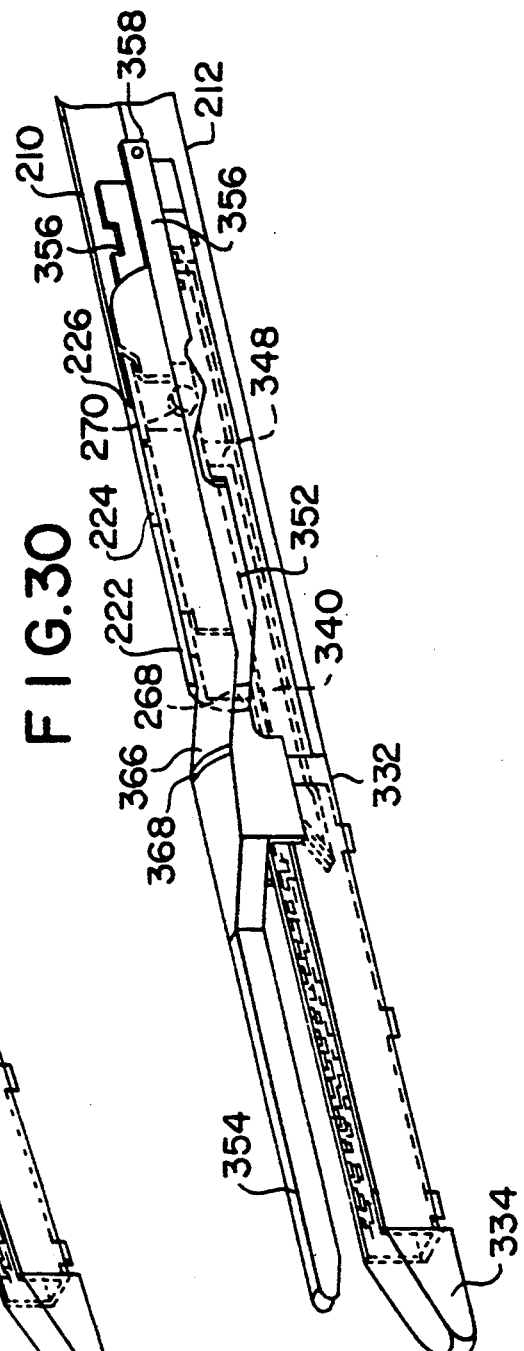

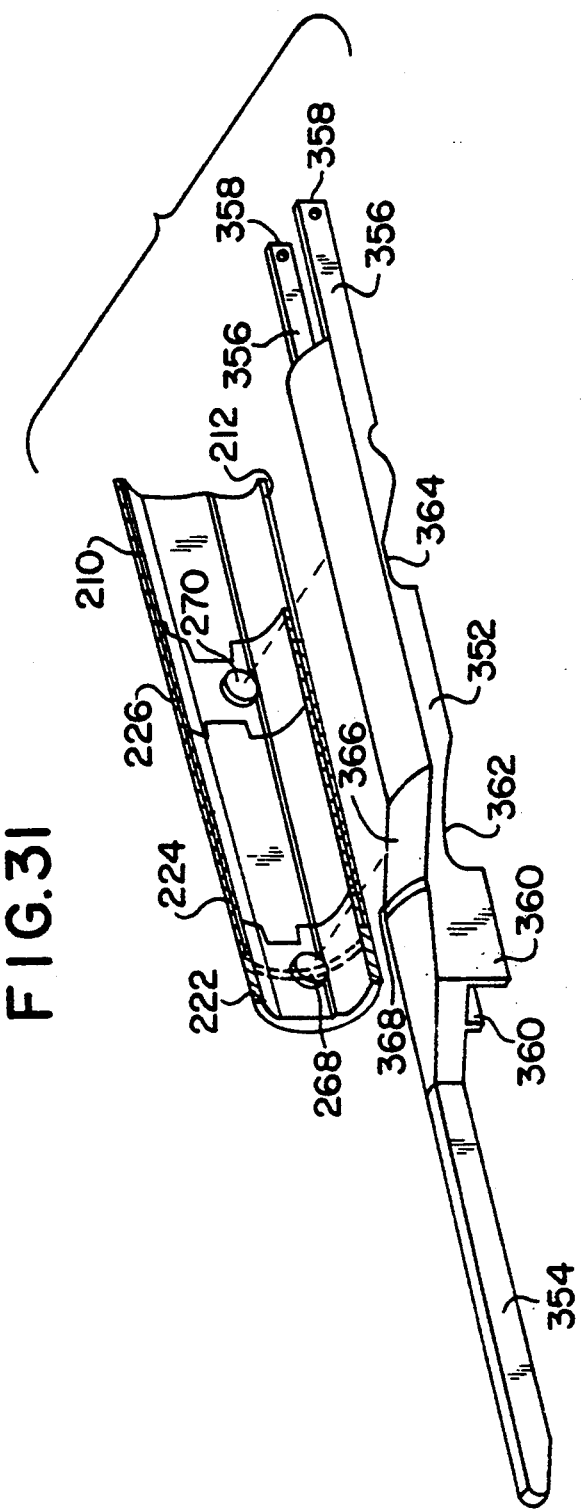

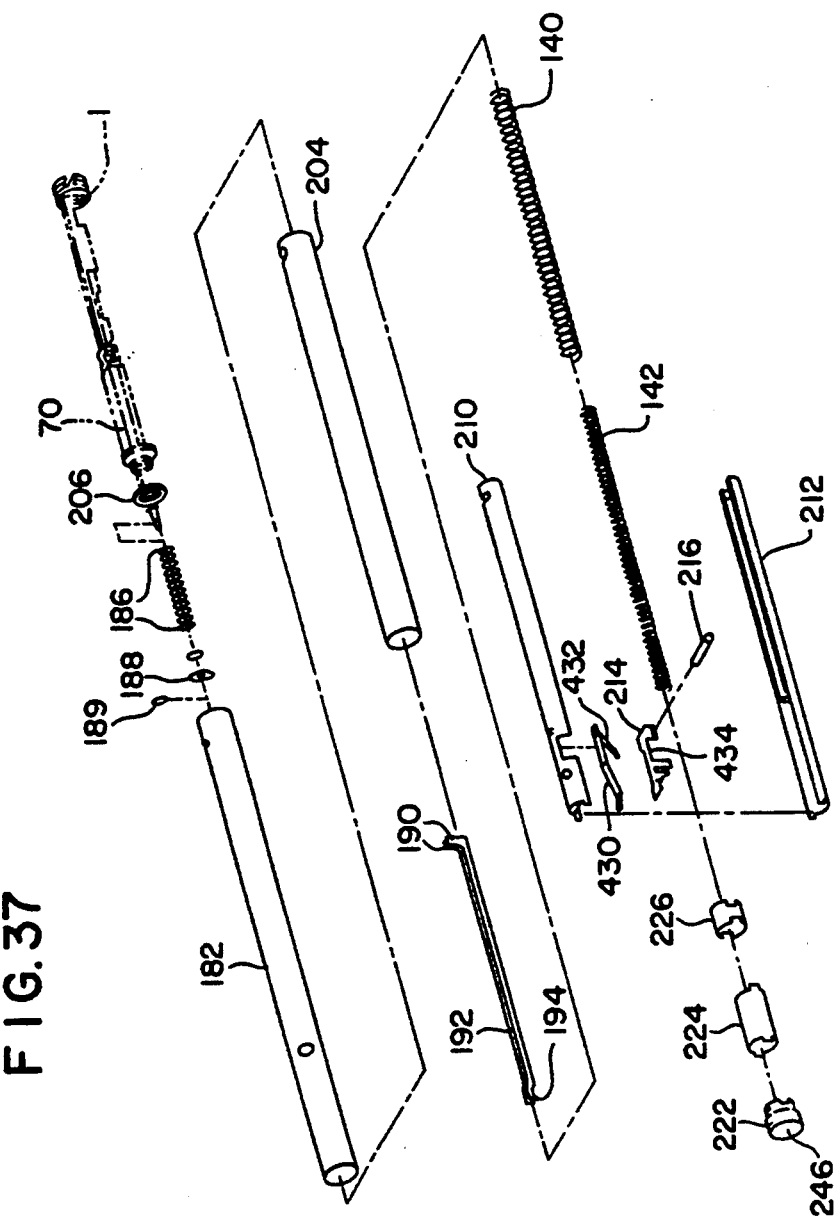
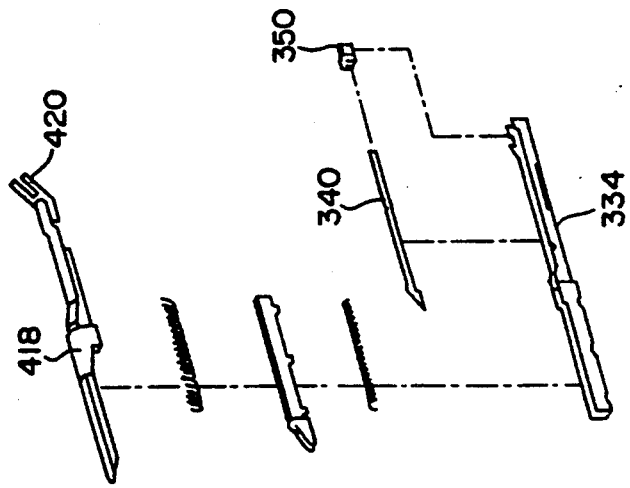
FIG. 37

SELF CONTAINED GAS POWERED SURGICAL APPARATUS

CROSS REFERENCE TO RELATED APPLICATIONS

This is a continuation of application Ser. No. 07/915,425 filed on Jul. 17, 1992, now abandoned which was a continuation of application Ser. No. 07/781,012 filed Oct. 18, 1991, now abandoned.

BACKGROUND OF THE INVENTION

1. Field of the Invention

This invention relates to surgical stapling apparatus, and more particularly to surgical apparatus which are powered by self contained relatively low pressure gas systems to perform sequential operations such as tissue clamping, staple forming and/or tissue cutting.

2. Description of Related Art

Surgical stapling apparatus is known wherein tissue is first grasped or clamped between opposing jaw structure and then fastened by means of fasteners.

In some instruments a knife is provided to cut tissue which has been joined. The fasteners are typically in the form of surgical staples however, two part polymeric type fasteners am also known.

Instruments for this purpose can comprise two elongated fingers which are respectively used to capture or clamp tissue. Typically, one of the fingers carries a disposable cartridge housing a plurality of staples arranged in at least two lateral rows while the other finger comprises an anvil for curling the staple legs into hook form upon their being driven against the anvil. The stapling operation is effected by a pusher which travels longitudinally along the cartridge carrying finger, with the pusher acting upon the staples to place rows of staples in body tissue. A knife may optionally be positioned to operate sequentially immediately behind the pusher and laterally positioned between the staple rows longitudinally cut and/or open the stapled tissue between the rows of staples. Such instruments are disclosed in Bobrov et at. (U.S. Pat. No. 3,079,606) and Green (U.S. Pat. No. 3,490,675). The instruments disclosed therein comprise apparatus for simultaneously making a longitudinal incision and applying a row of staples on both sides of an incision.

A later development disclosed in Green (U.S. Pat. No. 3,499,591) applies a double row of staples on each side of the incision. This is accomplished by a cartridge assembly wherein a cam member moves within a guide path between two sets of staggered staple carrying grooves. Staple drive members located within the grooves each have two staple pusher plates, and sloping surfaces disposed within the guide path so as to be contacted by the longitudinally moving cam and be driven along the groove to effect ejection of two staples.

The cartridge assemblies typically come in a plurality of sizes, each varying in both length and number of staples contained therein. Depending on the procedure to be performed, the surgeon must select the appropriate cartridge assembly. No provision is currently available to adjust the firing means of the instrument itself so that a wide variety of staple driving sequences may be accomplished using a single staple cartridge assembly.

The instruments described above were all designed to be used in surgical procedures wherein surgeons have direct manual access to the operation site. However, in endoscopic or laparoscopic procedures surgery is performed through a small incision or through narrow cannulae inserted through small entrance wounds in the skin. In order to address the specific needs of endoscopic and/or laparoscopic surgical procedures, an endoscopic surgical stapling apparatus such as that shown in Green et al. (U.S. Pat. No. 5,040,715) has been developed. This apparatus is well suited for such procedures and incorporates a distal end having an anvil and staple cartridge assembly and a manually operated handle assembly interconnected by an endoscopic portion which permits the instrument to be inserted into a cannula and be remotely operated by the surgeon.

The instruments discussed above all require some degree of manually applied force in order to clamp, fasten and/or cut tissue. This manual application can prove awkward or difficult depending upon the orientation of the instrument relative to the surgeon, the type of tissue being operated on or the strength of the surgeon. Furthermore, because of the difficulty and expense of cleaning and sterilizing surgical instruments between uses, there is increasing interest in and demand for instruments which are disposable after use in a single surgical procedure rather than permanent and reusable. And because of the greater convenience and ease of using self-powered instruments as well as the more uniform results typically produced by self-powered instruments (as compared especially to manually powered instruments), there is increasing interest in and demand for instruments which are self-powered. Accordingly, there is a need for a self-powered endoscopic surgical apparatus to alleviate these difficulties.

Self contained gas powered surgical staplers are known, as shown, for example, in U.S. Pat. Nos. 3,618,842; 3,643,851; 3,662,939; 3,717,294; 3,815,476; and 3,837,555. Typically, these staplers include a replaceable cylinder which supplies gas (e.g., carbon dioxide or nitrogen) at relatively high pressure (e.g., 800 p.s.i.g.) for powering the instrument. The high pressure gas used in these staplers requires that the staplers be of relatively heavy construction in order to safely accommodate the high pressure involved. Because of their construction, these instruments are relatively expensive to manufacture and therefore generally intended to be relatively permanent and reusable.

Use of a relatively low pressure gas is advantageous to enable a stapler to be made of lighter construction and less expensive materials. This is desirable to lower the cost and make the stapler economically disposable. The stapler must, however, be capable of generating the substantial forces required to form the staples. Typically, the staples are metal wire which is partially formed prior to use and which must be further formed (e.g., crimped against an anvil) by the stapler. To generate the relatively large forces required to form the staples with low pressure gas would ordinarily require a relatively large pneumatic actuator. This is undesirable because a large actuator makes the stapler bulky and difficult to work with. In addition, a large actuator unnecessarily consumes a large amount of gas during the portion of actuator motion when relatively large forces are not required, i.e., during the first part of the actuator stroke when the staple is merely being advanced to the staple forming position. The gas which is thus effectively wasted substantially reduces the number of stapling operations which can be performed by the stapler before its gas supply is exhausted. This substantially shortens the useful life of the stapler if the gas supply is not replaceable, and even if the gas supply is replaceable, it undesirably increases the frequency with which the gas supply must be replaced.

Although it is desirable to perform most of the functions of the stapling apparatus automatically using self-powering elements in the apparatus, it may also be desirable for the initial function to be at least partly manual. For example, if the initial function is tissue clamping, it is preferably initiated manually so that it can be performed slowly and precisely and the results inspected and corrected if necessary before the automatic self-powered portion of the operating sequence begins. See, for example, U.S. Pat. Nos. 4,349,028 and 4,331,277 to Green.

Accordingly, there is a present need for a self contained gas powered surgical instrument for driving surgical fasteners into body tissue which instrument can be made of lighter materials and can be made disposable after use.

Because endoscopic procedures are more common than laparoscopic procedures, the present invention shall be discussed in terms of endoscopic procedures and apparatus. However, use herein of terms such as "endoscopic", "endoscopically" and "endoscopic portion", among others, should not be construed to limit the present invention to a stapling and cutting apparatus for use only in conjunction with an endoscopic tube. To the contrary, it is believed the present invention may find use in any procedure where access is limited to a small incision, including but not limited to laparoscopic procedures. Also, as used herein the terms "fasteners" and "staples" shall be treated equivalently. Unless otherwise stated, the term "cartridge assembly" shall include at least the cartridge itself and staples or fasteners and staple drive members disposed therein.

OBJECTS OF THE INVENTION

Accordingly, it is one object of the present invention to provide a self contained gas powered surgical apparatus for driving fasteners into body tissue.

It is another object of the present invention to provide a self contained endoscopic surgical apparatus which is powered by a low pressure pneumatic system contained within the apparatus.

It is yet a further object of the present invention to provide a self contained gas powered surgical apparatus insenable through a small incision or narrow tube for driving surgical fasteners into body tissue and cutting the body tissue between rows of staples.

Another object of the present invention is to provide a self contained gas powered surgical apparatus which is disposable after use.

A further object of the present invention is to provide a self contained gas powered surgical apparatus which may be selectively set to drive surgical fasteners in a variety of sequences.

Another object of the present invention is to provide a self contained gas powered surgical apparatus which is activatable to move through an entire sequence of operation by a single press of the actuator.

A further object of the present invention is to provide a self contained gas powered surgical apparatus having a gas metering element to prevent firing of the staples from the cartridge unless a sufficient quantity of gas is available to move the driving member through a full sequence of operation.

Another object of the present invention is to provide a self contained gas powered surgical apparatus having a clamping lockout mechanism which will prevent clamping of tissue unless the cartridge has been properly inserted in the instrument.

A further object of the present invention is to provide a self contained gas powered surgical apparatus having sealing structure for inhibiting the escape of gas through the apparatus.

Another object of the present invention is to provide a self contained gas powered surgical apparatus having counter structure for displaying the number of times the instrument has been fired.

A further object of the present invention is to provide a self contained gas powered surgical apparatus with lockout structure to disable the apparatus after a predetermined number of firings.

SUMMARY OF THE INVENTION

These and other objects of the invention are accomplished in accordance with the principles of the invention by providing a self contained endoscopic surgical instrument which is at least partially operable by means of a relatively low pressure pneumatic assembly. Advantageously, the surgical instrument in accordance with an embodiment of the present invention is a surgical stapling apparatus adapted for placing one or more longitudinal rows of staples. This apparatus may further include a knife for making an incision in body tissue between rows of staples. The latter configuration may find particular use of adjoining two hollow organs or in removing an organ, such as the appendix, the gallbladder, etc.

The self contained gas powered surgical instrument of the present invention in an endoscopic stapler configuration comprises a frame; an endoscopic portion defining a longitudinal axis and extending distally from the frame, the endoscopic portion including an elongated housing having a distal member for mounting a cartridge assembly. The cartridge assembly includes a plurality of surgical staples slidably mounted therein and has a tissue engaging surface. An anvil member is also provided and has a staple forming surface and a proximal end mounted to the elongated housing such that the anvil member is movable between an open position and a closed position such that the staple forming surface is in close cooperative alignment with the tissue engaging surface of the cartridge assembly.

The instrument further includes structure for moving the anvil member between the open and the closed positions and structure for ejecting the surgical staples from the cartridge assembly to cause the staples to engage and form on the staple forming surface of the anvil member.

A self contained pneumatic system is disposed in the frame and includes a supply of relatively low pressure gas connected to a pneumatic actuator mechanism. The pneumatic actuator mechanism actuates the structure for ejecting the surgical staples from the cartridge assembly.

The surgical instrument may be constructed either as a reusable unit or as a single use, disposable unit or, alternatively may be formed with a reusable handle portion and replaceable staple carrying cartridges.

The present invention advantageously permits surgeons to perform internal surgical procedures including stapling and/or cutting simply by manually clamping the tissue to be manipulated and pneumatically actuating the jaw members. This results in greater convenience and ease of use of the instrument as well as more uniform actuation of the instrument mechanisms.

The stapler embodiment of this invention is preferably controlled by a manually operable trigger or other similar control. Momentary operation of the trigger initiates an operating cycle of the stapler which normally is automatically completed without continued actuation of the trigger. A safety interlock may also be employed in cooperation with the trigger mechanism to prevent accidental actuation. Preferably the stapler performs only one operating cycle in response to each operation of the control regardless of the length of time the control is operated beyond the time required to initiate an operating cycle. The stapler also cannot begin a new operating cycle until the preceding cycle is complete. Also, a safety mechanism may be incorporated to prevent closure of the jaws if they are misaligned or improperly inserted. In a particularly preferred embodiment of the invention, the operating cycle will not begin unless sufficient gas remains in the reservoir to propel the instrument through a complete cycle. Alternatively, structure may be provided to give a visual or tactile indication of the number of times the instrument has been fired and/or lock out the operating cycle after a given number of firings. Sealing means may be provided to more efficiently seal the apparatus and prevent excess gas from passing through the interior thereof.

In another particularly advantageous embodiment of the invention the surgical element includes adjustment structure which permits the instrument to be selectively preset to fire in a predetermined sequence to drive a given number of staples and/or rows of staples.

Further features of the invention, its nature and various advantages will be more apparent from the accompanying drawing and the following detailed description of the invention.

BRIEF DESCRIPTION OF THE DRAWINGS

Preferred embodiments of the invention are described hereinbelow with reference to the drawings. In the drawings and the description which follows, "proximal" means the end closest to the operator and "distal" means the end furthest from the operator.

FIG. 3A is a side plan view in partial cut away of the pusher washers and flange member of the pneumatic system in accordance with one embodiment of the present invention;

FIG. 9 is a top plan view in cross section taken along line 9—9 of FIG. 5 showing the frame and pneumatic assembly of the surgical instrument;

FIG. 10 is a transverse view in cross section taken along line 10—10 of FIG. 5 oriented toward the distal end of the instrument showing a portion of the frame and pneumatic assembly;

FIG. 12 is a side cut away view in cross section showing the operation of the pneumatic assembly of the present invention as it is fired;

FIG. 13 is a side cut away view in cross section taken along line 13—13 of FIG. 12 showing the valve and gas tube of the pneumatic assembly;

FIG. 14 is a side plan view in cross section showing the frame and pneumatic assembly of a surgical instrument incorporating an adjustable stroke mechanism;

FIG. 16 is a side plan view of a channel member in accordance with one embodiment of the present invention;

FIG. 17 is a transverse view in cross section taken along line 17—17 of FIG. 16 oriented toward the proximal end of the channel member;

FIG. 18 is a transverse view in cross section taken along line 18—18 of FIG. 16 oriented toward the distal end of the channel member;

FIG. 19 is a bottom plan view of an anvil member in accordance with one embodiment of the present invention;

FIG. 20 is a top plan view of the anvil member of FIG. 19;

FIG. 21 is a side view of the anvil member of FIG. 19;

FIG. 25 is a side plan view in cross section of the cartridge housing of FIG. 4;

FIG. 26 is a top plan view of the cartridge housing shown in FIG. 25;

FIG. 27 is a side cut away view in cross section of the cartridge housing of FIG. 25 taken along line 27—27 of FIG. 26;

FIG. 28 is an exploded perspective view of another embodiment of the cartridge assembly of the surgical instrument in accordance with the present invention;

FIG. 29 is a perspective view of the assembled cartridge assembly of FIG. 28;

FIG. 30 is a perspective view in partial cross section of an anvil and cartridge assembly in accordance with the present invention;

FIG. 31 is a perspective view in partial cross section of an anvil in accordance with the embodiment of FIG. 30;

FIG. 37 is an exploded perspective view of the endoscopic portion and jaw structure of the self contained gas powered surgical instrument of FIG. 35;

DETAILED DESCRIPTION OF THE PREFERRED EMBODIMENTS

Although the principles of the invention are applicable to other types of self contained gas powered surgical fastening instruments, the invention will be fully understood from the following illustration of its application to endoscopic surgical fastening instruments of the type shown, for example, in Green et al. U.S. Pat. No. 5,040,715. Also, although the invention is applicable to surgical fastening apparatus having other constructions, the invention will be illustratively described in its application to surgical staplers in which a staple cartridge containing a plurality of staples, staple drivers and staple firing means in cooperation with anvil means respectively form opposing jaw structure located on a distal end of the stapler for capturing and joining tissue.

I. Overall Construction and Operation of the Firing Assembly

Figure 1:
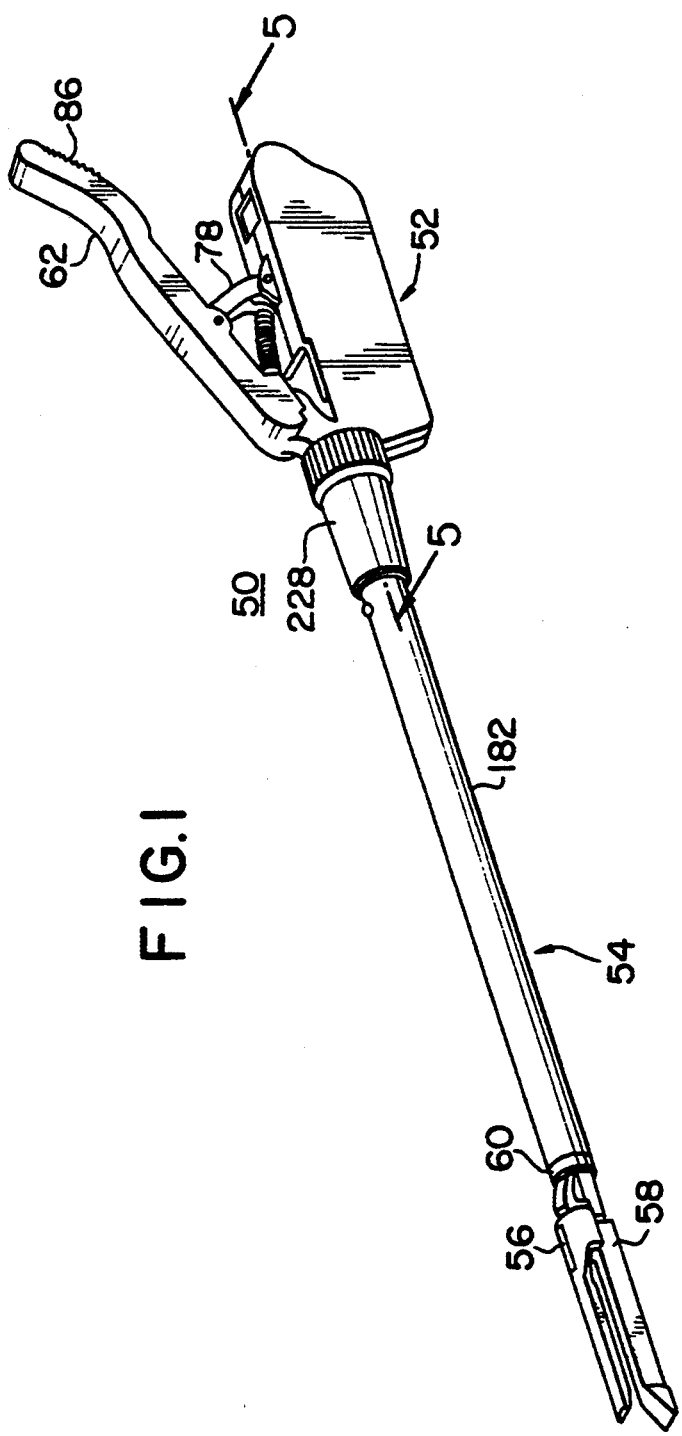
FIG. 1 is a perspective view of a self contained gas powered endoscopic surgical instrument in accordance with one embodiment of the present invention.

As shown in FIG. 1, a self contained gas powered endoscopic surgical instrument 50 constructed in accordance with the principles of this invention includes a frame 52 and an endoscopic portion 54. An anvil 56 and cartridge assembly 58 are mounted in a distal end 60 of endoscopic portion 54 and are preferably interchangeable with other anvil/cartridge assemblies (as discussed in greater detail hereinbelow) to perform a wide variety of surgical fastening procedures as needed.

Anvil 56 and cartridge assembly 60 are manually controlled by means of an articulating handle 62 in the frame 52. This handle 62 interconnects with anvil 56 by means of a linkage disposed in endoscopic portion 54 such that when handle 62 is moved from its open position (FIG. 1) to a closed position (FIG. 7), anvil 56 is moved into close approximation with cartridge assembly 58. This operation will be discussed in greater detail below.

Figure 2:
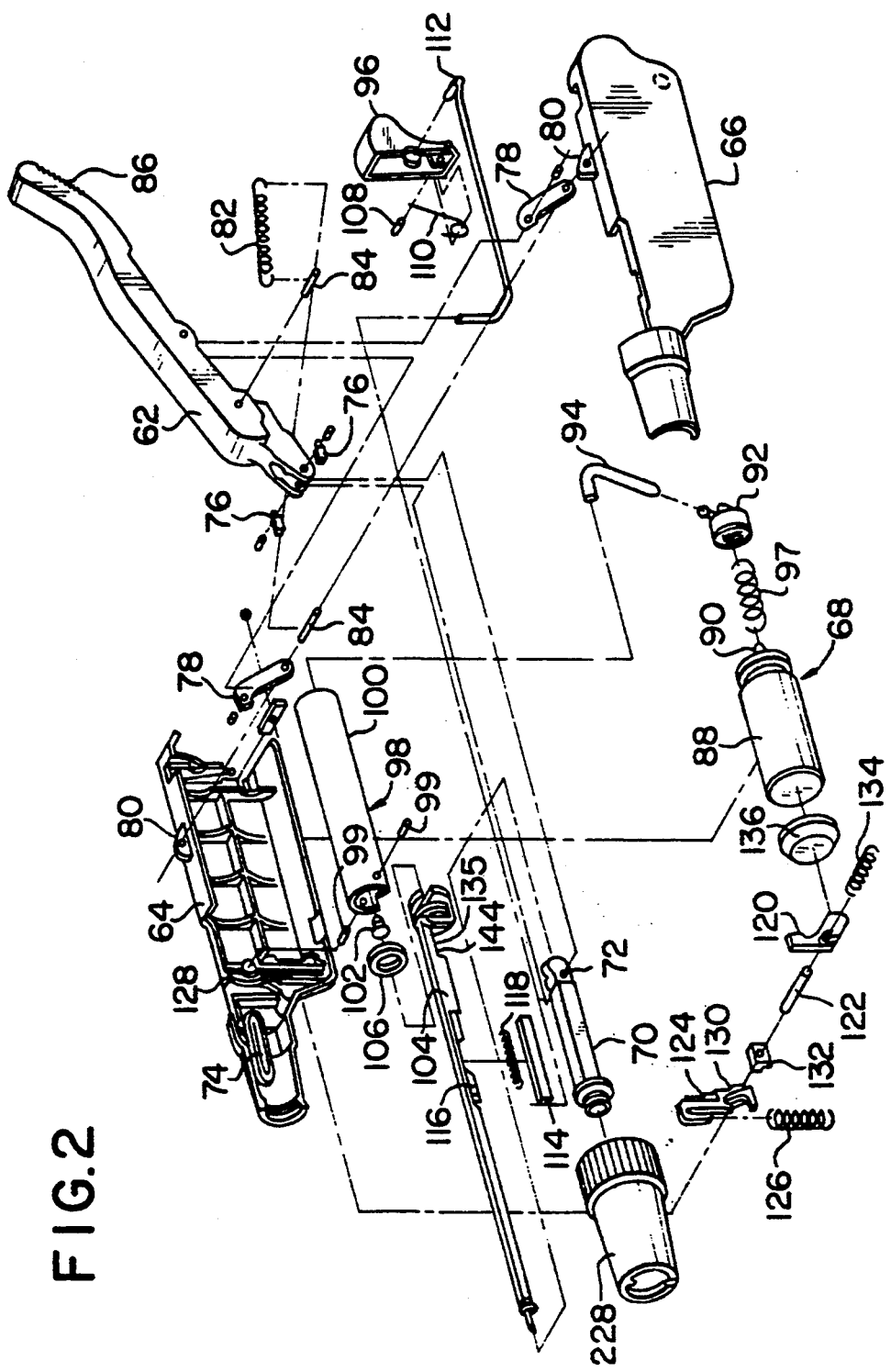
FIG. 2 is an exploded perspective view of the frame and pneumatic assembly of the surgical instrument of FIG. 1.

Turning now to FIG. 2, an exploded perspective view of the frame and pneumatic system is shown in accordance with the present invention. Frame 52 includes a first housing member 64 and a second housing member 66 enclosing a pneumatic system shown generally at 68. Articulating handle 62 is pivotally connected at a distal end thereof to clamp tube 70 at pivot point 72. Longitudinal grooves 74 formed in both first and second housing members 64, 66 adjacent pivot point 72 slidably receive molded shuttles 76 attached to handle 62 at 72. The molded shuttles 76 are pivotally connected to either side of the pivot point 72 on the distal end of handle 62 and serve to guide the distal end of handle 62 in a longitudinally distal direction as the handle is compressed.

A pair of articulating links 78 interconnect an intermediate portion of handle 62 to a pair of projections 80 formed on an upper surface of housing members 64, 66 respectively. A handle return spring 82 extends between handle 62 and housing members 64, 66 by means of spring anchor pins 84, one of which is disposed in handle 62 and the other extending between projections 80 which also serve to pivotally connect articulating links 78 to projections 80. This spring 82 assists in returning handle 62 from its closed position to its open position.

The proximal end of handle 62 is preferably diagonally formed away from housing members 64, 66 so as to enable the surgeon to more easily release the handle 62 from its closed position. This is done by placing the hand under the proximal end of the handle and lifting. A texturized or serrated portion 86 may advantageously be formed on an under surface of the proximal end of handle 62 to enhance gripping of the handle 62.

Pneumatic system 68 is wholly contained within housing members 64, 66 and includes a container 88 of relatively low pressure gas longitudinally slidably mounted therein. The pressure of the gas in container 88 during operation of the stapler is typically less than about 200 p.s.i.g. and preferably in the range from about 80 p.s.i.g. to about 160 p.s.i.g. Any suitable non-toxic gas can be used including but not limited to halogenated hydrocarbons which are gaseous at room temperature, e.g., fluorinated hydrocarbons such as Freon 12 or chlorinated hydrocarbons such as Freon 152A. Container 88 dispenses the relatively low pressure gas through stem 90, valve 92 and gas tube 94 when the firing trigger 96 is depressed. Spring 97 is positioned between container 88 and valve 92 and serves to hold the container 88 away from valve 92. Valve 92 is fixed within housing members 64, 66 and is longitudinally adjustable by means of set screw 93. (FIG. 13) This feature permits the position of valve 92 to be longitudinally changed to compensate for manufacturers' variations in length among containers 88 between a distal end and the proximal end of stem 90.

Disposed above container 88 within housing members 64, 66 is a pneumatic actuator 98. Actuator 98 includes a pneumatic cylinder 100 which is held in place by opposing pins 99 and which is closed at its proximal end except for ferrule 102 and is open at its distal end, as well as a pneumatic piston 104 mounted for reciprocal motion in cylinder 100 parallel to the longitudinal axis of endoscopic portion 54. Cylinder 100 is preferably circular in transverse cross-section however other shapes would function acceptably well.

Piston 104 is pneumatically sealed to cylinder 100 by "O" ring 106 molded of polyethylene or the like. Gas dispensed from container 88 is supplied to pneumatic actuator 98 via gas tube 94 which admits the gas to cylinder 100 through ferrule 102 behind piston 104 to drive piston 104 distally in the cylinder. The distal end of piston 104 is adapted to engage the firing mechanism of the surgical apparatus as will be described in greater detail below.

Figure 5:
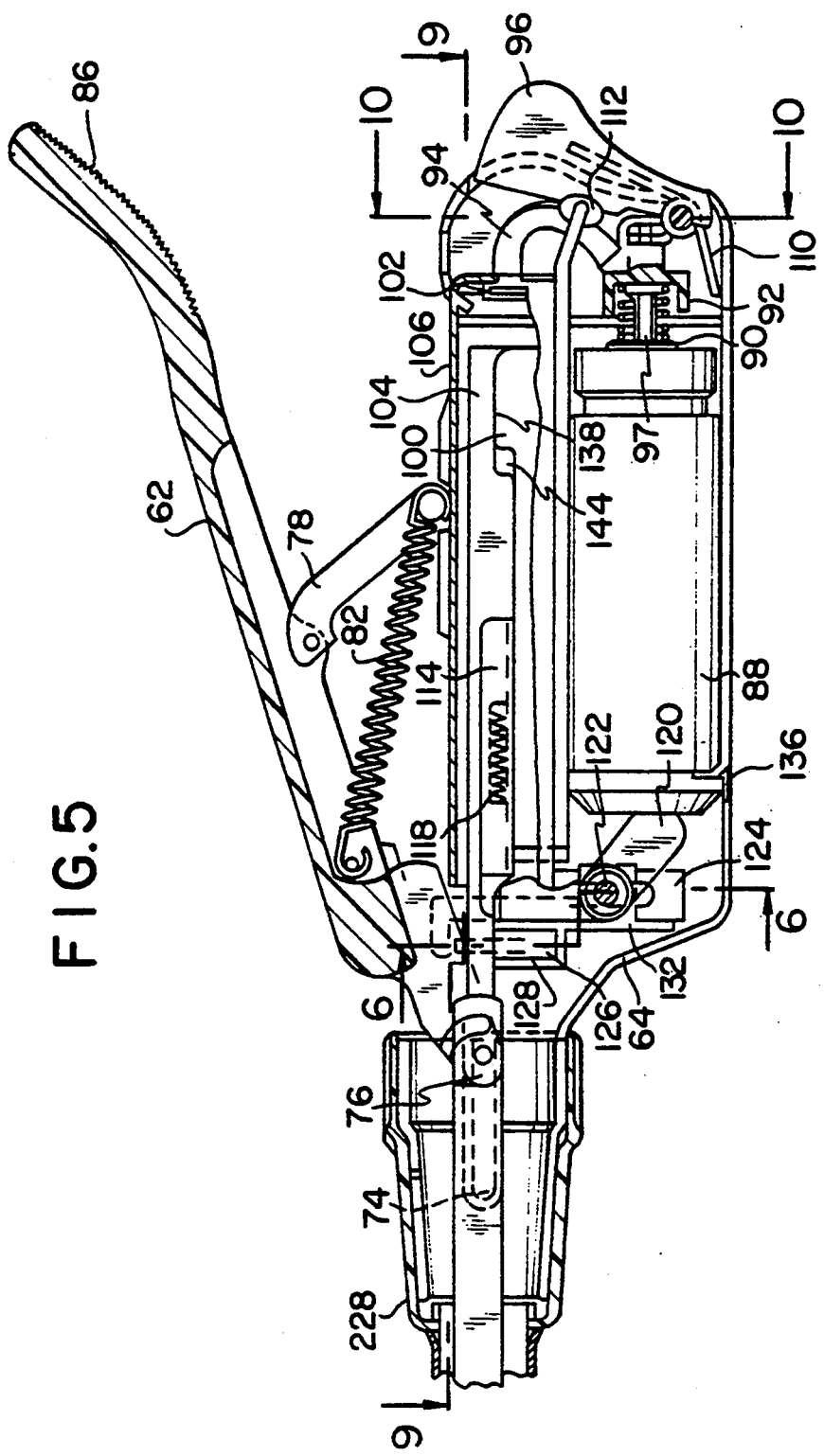
FIG. 5 is a side plan view in cross section taken along line 5—5 of FIG. 1 showing the frame and pneumatic assembly in the unclamped and unfired position.
Figure 7:
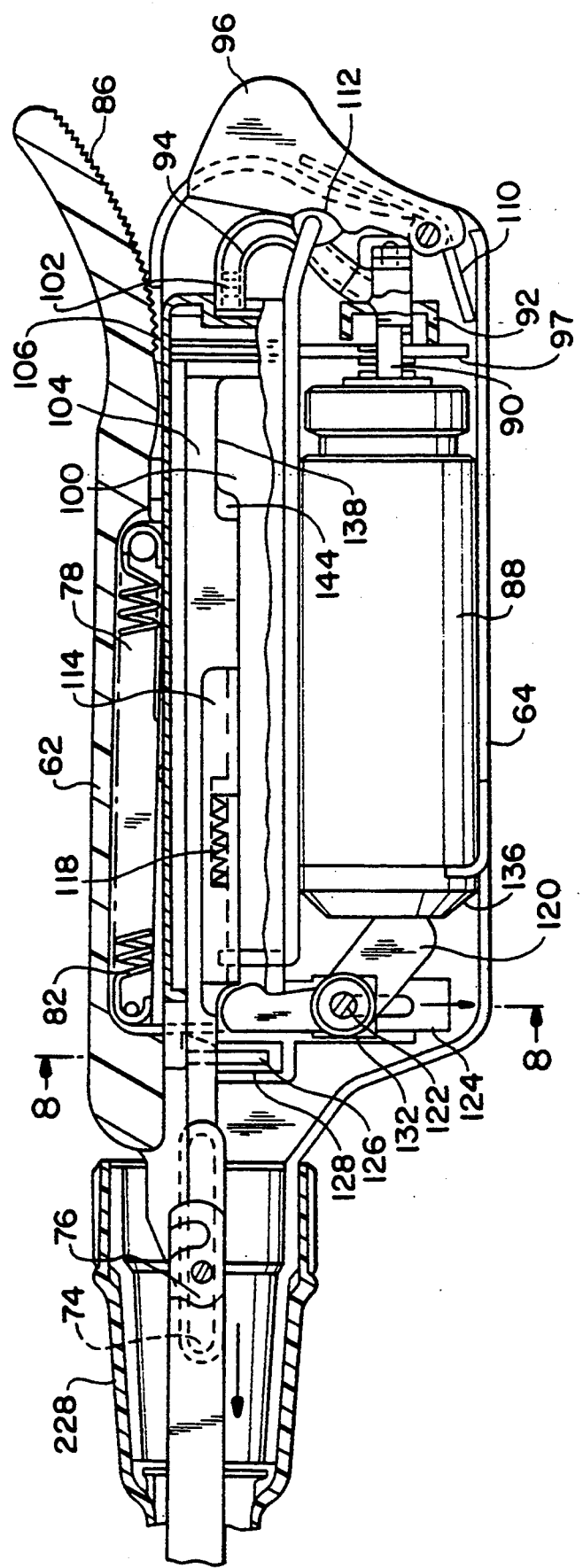
FIG. 7 is a side plan view in cross section showing the frame and pneumatic assembly in the clamped and unfired position.
Figure 11:
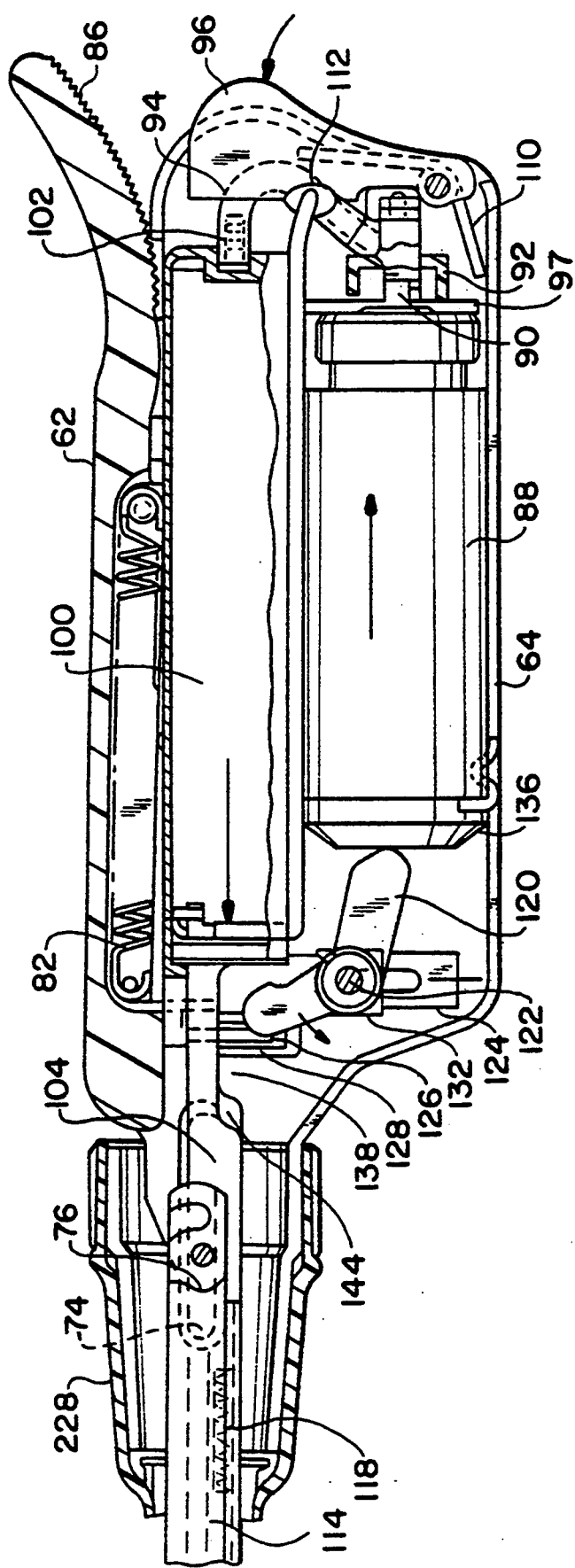
FIG. 11 is a side plan view in cross section showing the frame and pneumatic assembly of the present invention in the clamped and fixed position.

Referring to FIGS. 2, 5 and 7, firing trigger 96 is pivotally mounted in a proximal end of housing member 64, 66 by pivot pin 108. Spring 110 is positioned adjacent pin 108 and serves to bias the firing trigger 96 proximally into the prefiring position. A trigger rod 112 extends distally from firing trigger 96 longitudinally to engage piston slide 114 positioned in a lower portion of piston 104. Piston slide 114 comprises a substantially "U"-shaped channel which fits into a corresponding groove 116 formed in piston 104. Piston slide 114 is spring loaded in a proximal direction by spring 118 and includes a transverse projection 120 on a lower distal end thereof which engages the distal end of trigger rod 112.

Figure 6:
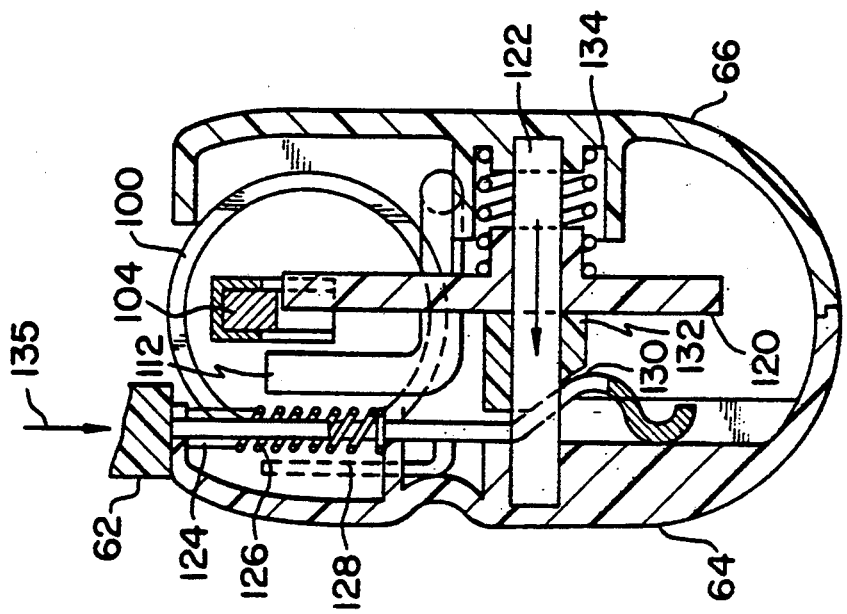
FIG. 6 is a transverse view in cross section taken along line 6—6 of FIG. 5 oriented toward the proximal end of the instrument showing the frame and pneumatic assembly in the unclamped position.

Referring now to FIGS. 2 and 5–11 and initially to FIGS. 2, 5–8 and 11, a rocking lever 120 is pivotally mounted on transverse slide pin 122 and is adapted for transverse movement relative to slide pin 122 between an engaged position prior to firing (FIGS. 7–9) and a disengaged position when articulating handle 62 is open (FIGS. 5 and 6). Cam slide 124 is vertically mounted in first housing member 64 for reciprocal movement between an upper and lower position (FIGS. 6 and 8 respectively) and serves to move rocking lever 120 between the engaged position (FIG. 8) and the disengaged position (FIG. 6). Thus, until the articulating handle 62 is closed causing cam slide 124 to move rocking lever 120 into the engaged position, the instrument 50 cannot be fired.

Figure 8:
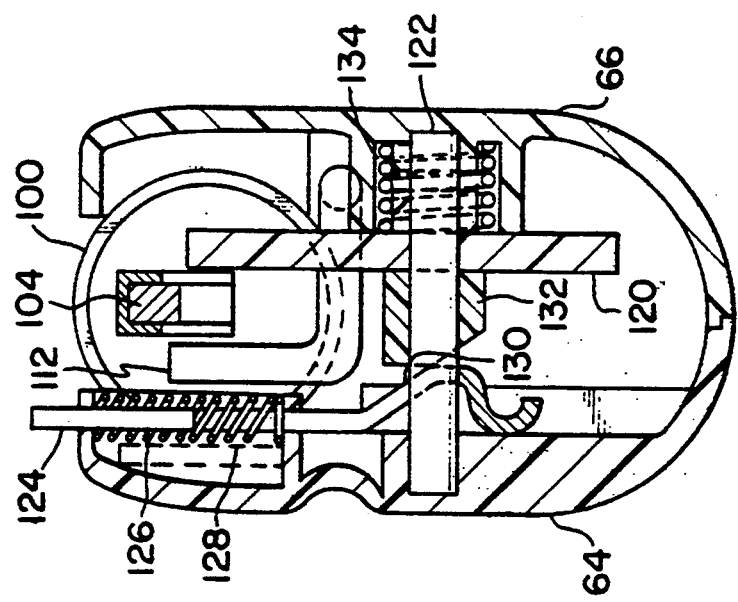
FIG. 8 is a transverse view in cross section taken along line 8—8 of FIG. 7 oriented toward the proximal end of the instrument showing the frame and pneumatic assembly in the clamped and unfired position.

Cam slide 124 is normally biased in its upper disengaged position by cam slide spring 126 mounted in vertical groove 128 of first housing member 64 (FIGS. 5 and 6). In this upper position, cam slide 124 extends upward beyond first housing member 64 (FIG. 6) to engage articulating handle 62 as it is moved to a closed position (FIGS. 7 and 8). Cam slide 124 further includes a camming surface 130 which contacts a corresponding camming surface of camming block 132 mounted on slide pin 122. Camming block 132 is loaded against cam slide 124 by slide spring 134 and moves rocking lever 120 transversely on slide pin 122 between an engaged position and a disengaged position. Referring to FIG. 8, as the articulating handle 62 is compressed toward housing members 64, 66 in the direction of arrow 135 it contacts cam slide 124 moving it downward and causes camming surface 130 to move camming block 132 and rocking lever 120 transversely into an engaged position in line with piston 104.

Turning to FIGS. 5, 7–9 and 11, once the articulating handle 62 has been fully compressed (FIGS. 7–9) rocking lever 120 is disposed in alignment with piston slide 114 and can be pivotally moved about transverse slide pin 122 to engage pusher disk 136 at the distal end of container 88. When the instrument is in the clamped configuration, depression of the firing trigger 96 moves trigger rod 112 distally in the longitudinal direction causing piston slide 144 to engage and pivot rocking lever 120 which, in turn, engages pusher disk 136 and moves container 88 longitudinally into contact with valve 92 to dispense gas and propel piston 104 in the distal direction. See FIGS. 11, 12 and 13.

As piston 104 moves distally, rocking lever 120 remains in its pivoted firing position by contact with the bottom surface of piston 104. A gap 138 is formed in the bottom surface of piston 104 near the proximal end thereof which gap effectively allows rocking lever 120 to disengage from piston 104 and pivot back to a position wherein container 88 is released from engagement with valve 92, stopping the flow of gas into pneumatic cylinder 100.

Return springs 140, 142 disposed in endoscopic portion 54 drive piston 104 back to its initial prefired position. A camming surface 144 is formed in a distal end of gap 138 and causes rocking lever 120 to move transversely out of engagement with piston 104 as it returns proximally and the rocking lever 120 moves to its original prefired position (FIG. 7).

FIG. 14 shows an alternate embodiment of the present invention incorporating an adjustment mechanism 146 which permits the instrument 148 to be selectively adjusted to change the length of the firing and return strokes of piston 150. This advantageous feature permits the user to selectively fire a predetermined length of staples using a single instrument. For example, if the user installs a staple cartridge assembly having six rows of staples, each row having a longitudinal length of 60 mm, the instrument is set using adjustment mechanism 146 to fire the staples in the entire length of the cartridge. Cartridges having some lesser length of staples may be inserted and fired depending on the needs of the user.

The adjustment mechanism 146 shown in FIG. 14 includes a belt 152 which travels around a pair of longitudinally disposed pulleys 154, 156. A first linkage rod 158 engages the top portion of belt 152 and extends to a gap adjustment member 160 slidably positioned in piston 150. A second linkage rod 162 engages the bottom portion of belt 152 and extends to a slidable piston stop 164 disposed within pneumatic cylinder 100.

Belt 152 may be rotated in either the clockwise or counterclockwise direction by rotating knob 166 disposed in housing 172 between pulleys 154 and 156. This permits the user to preselect the firing stroke of the instrument 148. For example when belt 152 is rotated counterclockwise, the firing stroke piston stop is being driven proximally by second linkage rod 162 and the gap 168 wherein the rocking lever 120 disengages the pneumatic actuator 98 is correspondingly widened. This permits the user to fire shorter rows of staples without changing cartridge assemblies. Conversely, when belt 152 is rotated in a clockwise direction, the firing stroke is progressively lengthened this allowing the user to fire up to the entire length of the rows of staples in the cartridge assembly.

In the instrument 148 shown in FIG. 14, the firing stroke may be preset to fire either 30 mm or 60 mm rows of staples from a 60 mm length cartridge assembly. These preset positions correspond to camming pins 186 and 170 respectively which serve to disengage first rod linkage 158 from belt 152 so that belt 152 is not rotated during the firing stroke of the pneumatic actuator 98.

Figure 15:
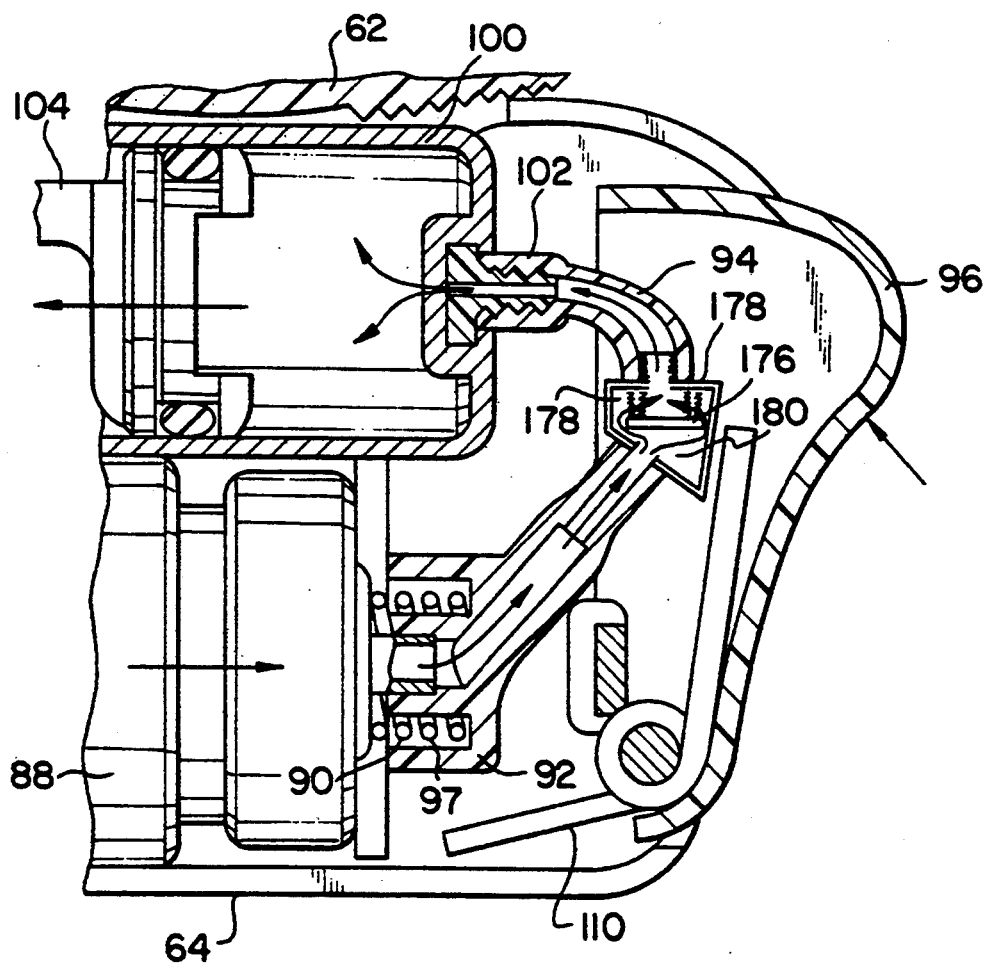
FIG. 15 is a side cut away view in cross section of a surgical instrument incorporating a metering assembly between the valve and piston assembly.

Turning now to FIG. 15, another beneficial feature is shown incorporated into the pneumatic system in accordance with the present invention. This feature comprises a pressure sensor 174 disposed in line between the valve 92 and the pneumatic cylinder 100 to sense and/or regulate the gas delivered from container 88 to the cylinder 100. During surgical procedures involving the driving of surgical fasteners and particularly where a knife is used to divide fastened tissue, it is important that when the trigger is depressed there is sufficient gas remaining in the container 88 to complete an entire piston firing stroke. If insufficient gas were available, the piston may not be able to fasten and/or divide the desired length of tissue, necessitating duplication of the procedure. Pressure sensor 174 serves to premeasure the amount of gas necessary to achieve the desired piston stroke before activating to permit the gas to flow into the pneumatic cylinder 100 to drive piston 104.

It is also envisaged that a counter mechanism can be incorporated to operate in conjunction with the pneumatic system 68 in order to monitor the number of firings which the instrument has been subjected to. This number can be visually displayed to the operator so that, for example, after a given number of firings, the instrument can be overhauled or replaced. Similarly, where a relatively small number of firings are available from a single gas container, this counter mechanism will assist the operator in recognizing when the container is nearing exhaustion. In a particularly desirable embodiment, the counter mechanism can be combined with a lockout mechanism which will disable the firing mechanism after a preselected number of firings.

As seen in FIG. 15, upon depressing firing trigger 96, gas is released from container 88 substantially as described hereinabove. However, after leaving stem 90 and passing through nozzle 92, the gas contacts pressure plate 176. Pressure plate 176 is preset by means of spring 178 to keep orifice 180 closed until a predetermined gas pressure is realized at the pressure plate 176. Once this threshold pressure is realized, pressure plate 176 moves out of contact with orifice 180 permitting gas to pass therethrough and into pneumatic cylinder 100 to drive piston 104 distally. In the event that insufficient gas is available to reach this threshold pressure, pressure plate 176 continues to block orifice 180 and the instrument cannot be fired.

Figure 3:
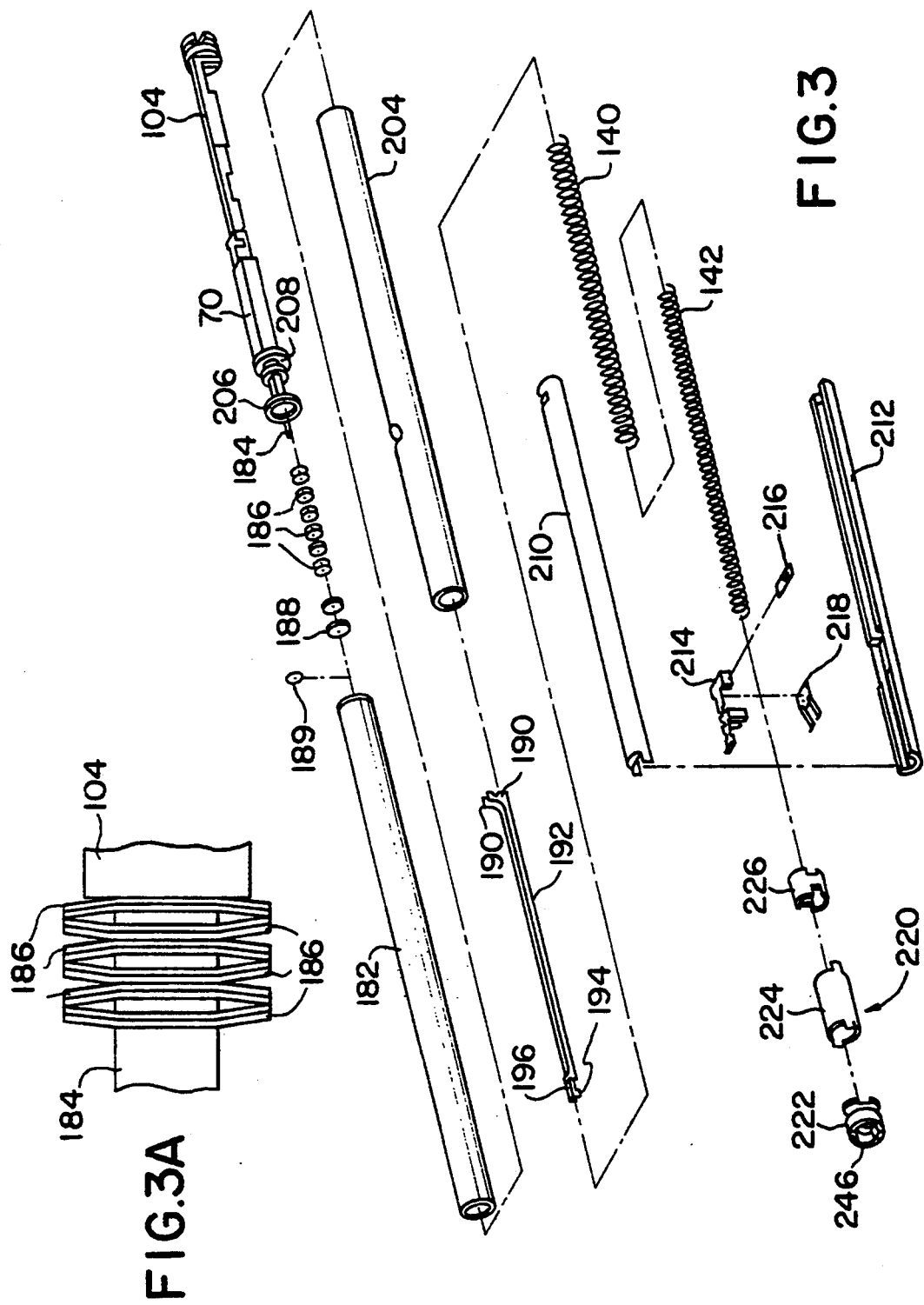
FIG. 3 is an exploded perspective view of the endoscopic portion of the surgical instrument of FIG. 1.
Figure 4:
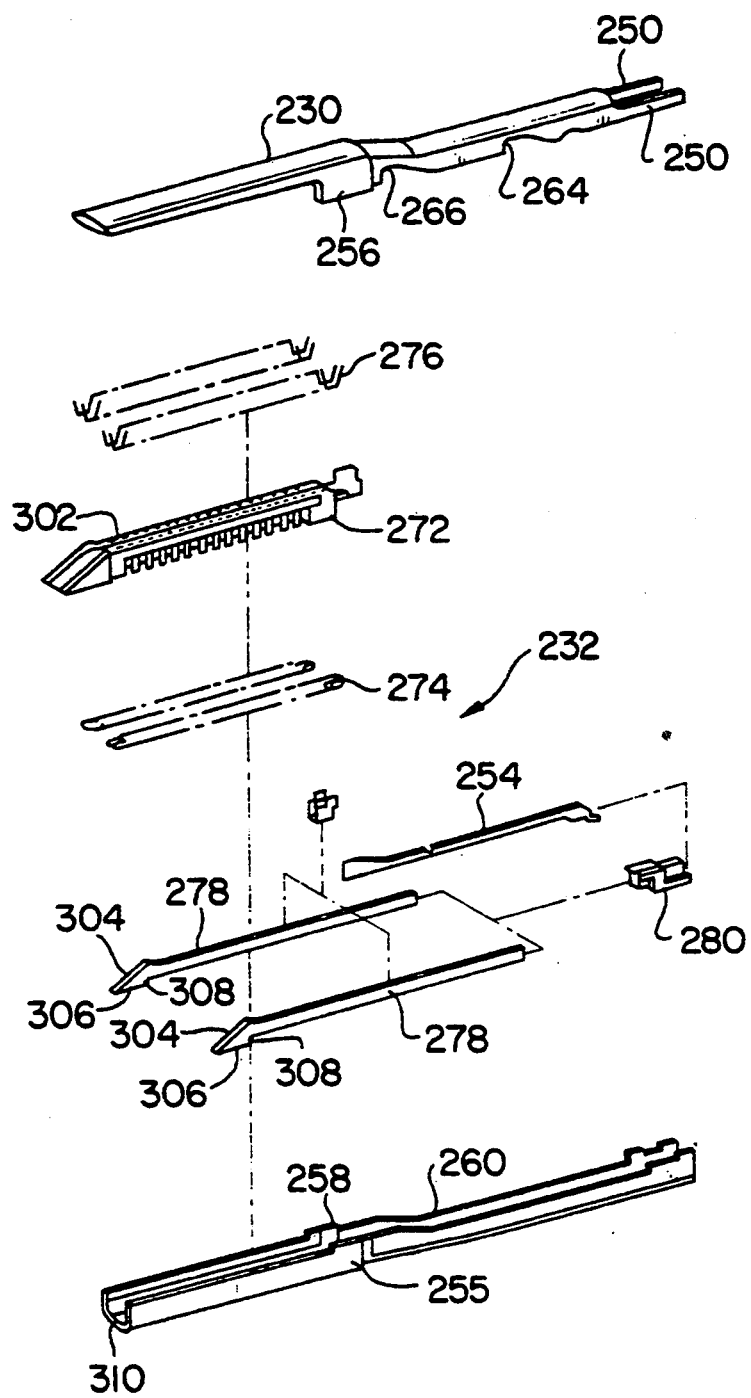
FIG. 4 is an exploded perspective view of one embodiment of the anvil and cartridge assembly of the surgical instrument of FIG. 1.

Referring now to FIG. 3, there is shown in exploded detail an endoscopic portion 54 in accordance with one embodiment of the present invention. At a proximal end, piston 104 is longitudinally reciprocally slidable through clamp tube 70 and extends into the proximal end of cover tube 182. The distal end of piston 104 is provided with an attachment flange 184 which flange 184 mounts a plurality of pusher washers 186 thereon. These pusher washers 186 are formed in a substantially abbreviated frustoconical cross-section from a resilient material such as, for example, commercial spring steel or type 302 stainless steel. These washers are typically known as Belleville Spring Washers available through SPEC Associated Spring Raymond, Barnes Group Inc. The washers are especially suited for high loads in small spaces and may be combined in varying sequences to achieve numerous load carrying possibilities. In the embodiment of FIG. 3, a total of twelve pusher washers are used substantially as shown in FIG. 3A with duplicate washers arranged in six opposing sets. A spring support washer 188 is positioned on flange 184 distal to pusher washers 186 and serves to engage the proximal ends of inner and outer return springs 140 and 142. Lock washer 189 holds the washers in place on flange 184. Attachment flange 184 has a chamfered distal tip and is configured and dimensioned to be received between the proximal fingers 190 and channel 192.

As shown in FIGS. 3 and 16–18, channel 192 is an elongated structure slidably mounted in endoscopic portion 54 for reciprocal longitudinal motion therein. As mentioned above, channel 192 has fingers 190 at a proximal end thereof to receive attachment flange 184 of piston 104. At a distal end of channel 192 there is provided a fork 194 defining a slot 196 therebetween. Fork 194 has a pair of opposed ramping surfaces, 198 and 200 respectively, the purposes of which will be described in greater detail below. Proximal to fork 194 is abutting structure 202 which structure extends below the lowermost dimension of fork 194.

Referring back to FIG. 3, an extension sleeve 204 is disposed within the cover tube 182 and is fixed on a proximal end thereof to clamp tube 70. Sealing member 206 is mounted on flange 208 of clamp tube 70 and serves to sealably isolate the frame 52 of the instrument 50 from the endoscopic portion 54. Inner and outer return springs, 142 and 140 respectively, are contained within upper extension spacer 210 and lower extension spacer 212 which are, in turn, fixed within the extension sleeve 204. Spring support washer 188 abuts the proximal ends of inner and outer return springs 142 and 140 and, when the instrument is fired, transmits the energy of the compressed springs 142, 140 to the piston 104, returning it to its prefired position.

Support structure 214 is also disposed within extension spacers 210, 212 and function to releasably receive anvil and/or cartridge assemblies in instrument 50. Support structure 214 is retained in place within extension spacers 210, 212 by transverse support key 216. An anvil return spring 218 is affixed to an underside portion of support structure 214 and assists in the retention of the anvil within the instrument.

A collar assembly, shown generally at 220, is attached to the respective distal ends of external sleeve 204 and extension spacers 210, 212. This assembly 220 includes a forward collar tube 222, a collar tube spacer 224 and a rear collar tube 226, each having camming bosses 268, 270 formed on inner surfaces therein as will be described in greater detail below.

In the embodiment of the present invention shown in FIGS. 1–3, the endoscopic portion 54 is rotatable relative to the frame 52 by means of rotation knob 228 (FIGS. 1 and 2). This rotation knob 228 is in the form of an abbreviated frustoconical structure having a bore therethrough dimensioned to receive a proximal end of cover tube 182. At a proximal end of knob 228, knurling 229 may be provided to facilitate rotation. Once connected to cover tube 182, rotation of knob 228 causes the distal working end of the instrument to rotate.

Referring now to FIGS. 4 and 19–27, there is illustrated an anvil 230 and cartridge assembly, shown generally at 232, in accordance with one embodiment of the present invention. Anvil 230 is an elongated piece which is mounted in support 214 by means of proximal legs 250. At its distal end, anvil 230 has an anvil plate 236 with a tissue contacting surface 238 having staple forming depressions 240 (See FIG. 19). At its proximal end, anvil 230 is provided with an upper camming surface 242 and locking surface 244, which surfaces are engagable with corresponding top arcuate camming surface 246 formed in forward collar tube 222. Transverse opposing projections 248 are formed on legs 250 at the proximal end of anvil 230 and provide an engagement point for anvil 230 to be cammed between an open and closed position by the interaction of camming surface 242, locking surface 244 and top arcuate camming surface 246 of collar tube 222. Preferably, the radius of curvature of the top arcuate camming surface 246 is shorter than the radius of curvature of camming surface 242 and equal to the radius of curvature of locking surface 244. This configuration prevents flexing of the camming surface 246 of collar tube 222 and lateral movement of the anvil as it is being cammed closed.

Anvil plate 230 also has a longitudinal center groove 252 to permit passage of a knife 254. Anvil 230 is further provided with parallel aligning surfaces 256 positioned below camming surface 242. These aligning surfaces are dimensioned to fit outside projections 258 on cartridge housing 260 upon closure of the anvil 230. The engagement of the aligning surfaces 256 and the corresponding projections 258 of cartridge housing 260 serves to more accurately and securely align anvil 230 and cartridge housing 260 upon closure. Further visual confirmation of alignment is facilitated by a pair of parallel longitudinal indentations 262 formed in the distal end of anvil 230. These indentations 262 allow the surgeon to view the closed structure of the anvil 230 and cartridge assembly 232 to confirm accurate longitudinal alignment thereof.

Further, as shown in FIG. 21, the horizontal plane formed by tissue contacting surface 238 intersects the horizontal plane formed by the camming portion of the proximal end of anvil 230 at an obtuse angle "$\alpha$". This angular orientation pre-cambers the anvil 230 and balances the closure force applied by the anvil 230 to the captured tissue.

First and second camming surfaces, 264 and 266 respectively, are formed in a sidewall portion of the proximal end of anvil 230. These camming surfaces engage camming bosses, 268 and 270 respectively, formed on inner opposing sidewalls of collar tube assembly 220. Anvil 230 is inserted into collar tube assembly 220 and projections 248 engage with support structure 2 14 bring camming surfaces 264 and 266 into engagable alignment with camming bosses 268 and 270. Cartridge assembly 232, discussed in greater detail hereinbelow, is fixedly inserted into collar tube assembly 220 and remains stationary relative to anvil 230.

During fabrication of anvil 230, the anvil blank may advantageously be formed by metal injection molding and thereafter coined and coated as described below. A wide variety of staples and fasteners are contemplated for use with the present apparatus. In a preferred embodiment for use with titanium fasteners, it has been found that forming of the fasteners in the staple forming depressions 240 is facilitated by applying a hard, relatively smooth surface on the staple forming portion of the anvil 230. The preferred method of application of this surface is by electroless plating, with the surface being formed of a metallic alloy such as, for example, nickel, gold, silver, titanium nitride or chromium. Where nickel is used, the applied surface is preferably in the range of $100\mu$-$2000\ \mu$ in thickness with an optimum thickness of between $200\mu$-$500\ \mu$. Ranges for other alloy may vary depending upon their inherent characteristics.

Where nickel is to be applied, the preferred method is an electroless plating method including the steps of: electrocleaning the anvil in a cyanide-containing cleaner, reversing polarity at predetermined intervals, preferably about every 10-15 seconds, at a current of about 50 amps/ft$^2$; rinsing thoroughly; rinsing in a solution containing a strong acid, preferably 20% HCL, dipping several times; immersing the anvil in a NiCL strike tank for plating, preferably for two to four minutes at a current of about 50 amps/ft$^2$; rinsing; and immersing the anvil in an electroless Ni bath, preferably Enthone 418 or 431, for a time sufficient to achieve the desired plating thickness. For example, at a deposition rate of 0.0005 in/hr, a time of between 30 to 40 minutes would be required to achieve a thickness of about $300\mu\pm50\ \mu$. Other coating procedures are also contemplated including vapor deposition, etc. and are encompassed by the present invention.

Turning now to FIGS. 4 and 22-27, there is illustrated a replaceable cartridge assembly 232 in accordance with the present invention. The cartridge assembly 232 includes: a cartridge housing 260; a cartridge 272 having a plurality of pushers 274 and staples 276 disposed in longitudinal arrangement therein; and a plurality of cam bars 278 removably disposed in cam bar adapter 280 and a cam bar alignment tab 282 as well as a knife 254 mounted in the cam bar adapter 280.

Referring specifically to FIGS. 25-27, the proximal end of cartridge housing 260 comprises a substantially elongate channel of semi-circular cross-section having a forward and rearward portion 284 and 286 respectively. A transverse locking slot 288 is formed in rearward portion 286 and serves to engage and retain support structure 214. Upon insertion into collar tube assembly, the forward end of support structure 2 14 is biased by the rearward portion 286 of cartridge housing 260 until the support structure 214 engages locking slot 288.

Figure 22:
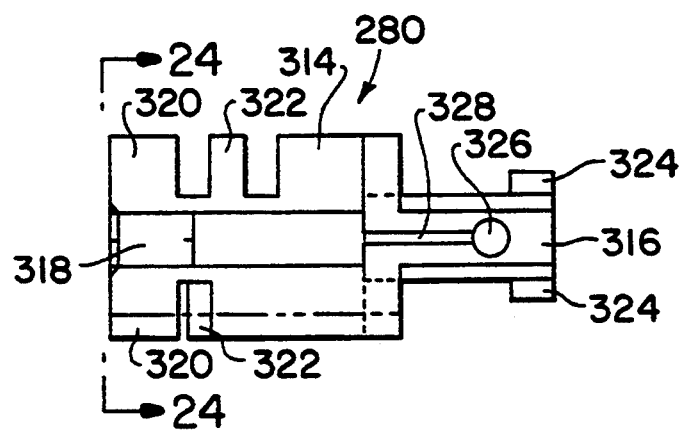
FIG. 22 is a top plan view of a cam bar adapter in accordance with one embodiment of the present invention.
Figure 23:
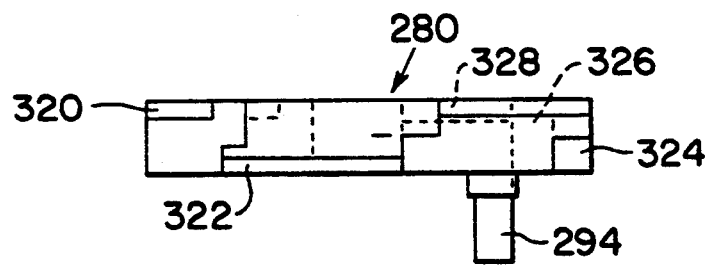
FIG. 23 is a side plan view of the cam bar adapter of FIG. 22.
Figure 24:
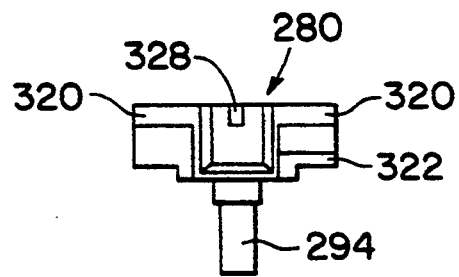
FIG. 24 is a from plan view of the cam bar adapter taken along line 24—24 of FIG. 22 oriented toward the proximal end of the adapter.

Rearward projection 290 is formed in the base of cartridge housing 260. The function of this projection 290 will be described in greater detail below. Forward of the projection 290 is a bore 292 which receives shear pin 294 formed on cam bar adapter 280 (FIGS. 22-24). A pair of crimps 296 is provided in opposing sidewalls of the rearward portion of the proximal end of the cartridge housing. These crimps 296 provide a friction fit with cam bar adapter 280.

The forward portion 284 of the proximal end of cartridge housing 260 has projections 258 which, upon closure of the cartridge assembly 232 and anvil 230, contact and align with anvil aligning surfaces 256 as described above.

The distal end of the cartridge housing 260 comprises a channel structure of substantially rectangular cross-section. This distal end constitutes the cartridge receiving portion and is dimensioned to receive cartridge 272 therein. Bores 298 and projection 300 serve to engage pins and bores respective in the cartridge 272 so as to align and retain the cartridge 272 within the cartridge receiving portion of the cartridge housing 260.

Referring to FIG. 26, the cartridge receiving portion in the distal end of cartridge housing 260 and the proximal end of cartridge housing 260 are joined at an obtuse angle 0 defined by the intersection of the horizontal planes of both the proximal and distal ends of the cartridge housing 260. This angular orientation serves to pre-camber the cartridge assembly and facilitates accurate closure and alignment of the jaw elements as well as more secure retention of subject tissue.

The cartridge 272 includes longitudinal groove structure 302 for receiving and guiding knife 254 and a plurality of pushers 274 abutting staples 276. The staples 276 are advantageously arranged in six longitudinal rows with three rows positioned on either side of groove structure 302.

Two pairs of longitudinal slots are formed in the cartridge housing 260 and are adapted to receive a pair of double cam bars 278 therein. Each pair of cam bars serving to drive three corresponding longitudinal rows of staples. Further, the two pairs of longitudinal slots extend to the end of cartridge 232.

Cam bars 278 are provided with a cam surface 304 in an upper distal end thereof and an overhanging ledge 306 with vertical surface 308 in a lower distal end. This overhanging ledge 306 is dimensioned to extend into the longitudinal slots to a point wherein the vertical surface 308 of the overhanging ledge 306 drops down and abuts the forward edge 310 of the cartridge retaining portion of the cartridge housing 260 when the cam bars 278 move to their distal fired position. At their proximal end, cam bars 278 are provided with hook structure 312 for releasably engaging cam bar adapter 280.

Referring now to FIGS. 22–24, there is shown multiple views of the cam bar adapter 280 in accordance with one embodiment of the present invention. The cam bar adapter 280 comprises a forward section 314 and a rearward section 316. The forward section 314 is substantially rectangular in shape and has a central longitudinal groove 318 formed therein and dimensioned to receive the longitudinal groove structure 302 therein when the cam bar adapter is urged to its forwardmost position. Flanges 320 and shelves 322 serve to removably retain the proximal end of cam bars 278.

The rearward section 316 is rectangular in shape with projections 324 formed in the proximal end thereof. The rearward section is dimensioned to be receivable within the slot formed in fork 194 in channel 192. The projections 324 are dimensioned to engage ramping surface 198 to allow the fork 194 to ride up and over the projections 324 when the fork 194 is moved in the distal direction.

Vertical bore 326 and longitudinal groove 328 are formed in the rearward section 316 and serve to retain and hold the shank of knife 254. Shear pin 294 is integrally formed with cam bar adapter 280 on a bottom surface thereof and, in the prefiring position, is aligned with and receivable into bore 292. Also, in this prefiring position, the rearward section 316 of the cam bar adapter 280 is disposed over rearward projection 290 to effectively shield engagement of abutting structure 202 with projection 290.

Turning now to FIGS. 28–34, there is shown a second preferred embodiment of an anvil and cartridge assembly in accordance with the present invention. Referring to FIGS. 28 and 29, the cartridge assembly 330 comprises a cartridge housing 332 mounting a cartridge 334 containing a plurality of pushers 336 disposed beneath staples 338, in a distal end thereof. A pair of cam bars 340 are positioned in the cartridge housing 332 and are adapted to move longitudinally through parallel longitudinal slots formed in cartridge 334. A camming surface 342 is formed on an upper distal end of cam bars 340 with an overhanging ledge 344 formed on a lower distal end. Vertical ledge 346 is formed proximal to overhanging ledge 344 and is adapted to engage the distal end of cartridge housing 332 when the cam bars 340 are driven to their full distal position. A cam bar alignment tab 348 engages both cam bars 340 and holds them in parallel alignment. A cam bar adapter 350 is adapted to fixedly receive the shank portion of cam bars 340.

Cartridge 334 is designed with three longitudinal rows of staples with each row of staples being offset from adjacent rows as shown in FIG. 28. This embodiment of the present invention does not utilize a knife structure and is designed to place rows of staples in body tissue.

Referring to FIGS. 30–31, an anvil 352 is shown having substantially the same design as anvil 230 described hereinabove with respect to the previous embodiment. The primary difference is that the distal portion 354 of anvil 352 is narrowed to receive and form three longitudinal rows of staples in contrast to the six rows of staples and knife accommodated by anvil 230. Anvil 352 includes a pair of longitudinally extending parallel legs 356 having transverse opposing projections 358. Parallel aligning surfaces 360 are formed in sidewalls of anvil 352 and serve to overfit and align anvil 352 on cartridge housing 332. First and second camming surfaces 362, 364 are formed in sidewalls of anvil 352 proximal to parallel aligning surfaces 360 and serve to engage camming bosses 268, 270 formed in forward collar tube 222 and rear collar tube 224, respectively.

Upper camming surface 366 is formed on an upper surface of anvil 352 proximal to distal end 354 with locking surface 368 formed distally adjacent upper camming surface 366. Both the upper camming surface 366 and the locking surface 368 are adapted to engage and be cammed by top arcuate camming surface 246 formed in the distal end of forward collar tube 222.

Figure 33:
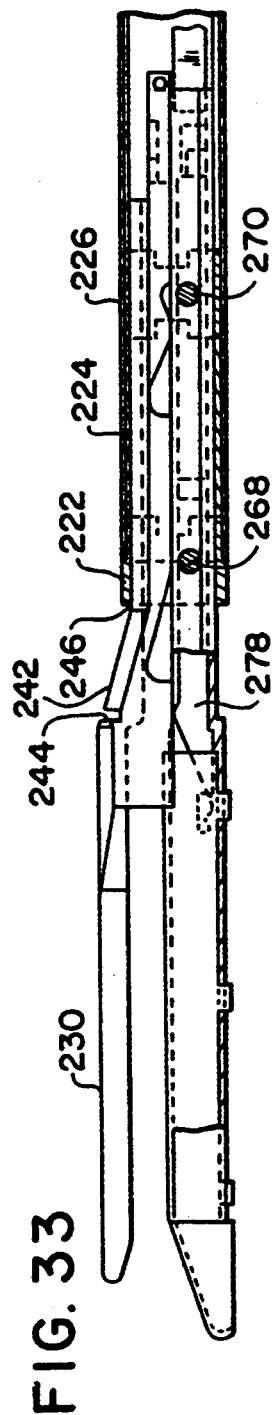
Figure 34:
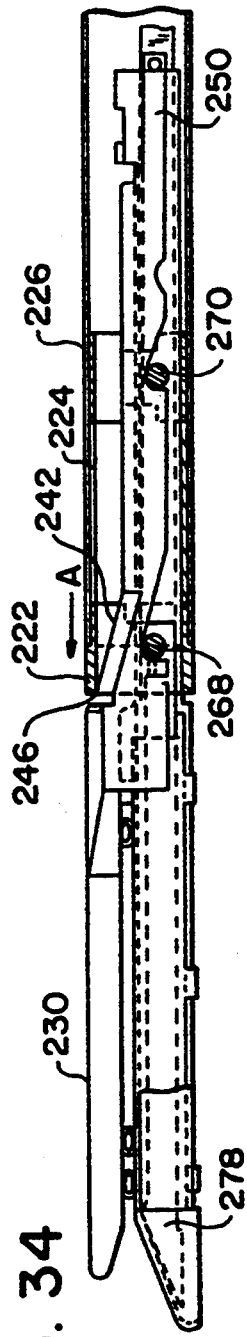
Figure 35:
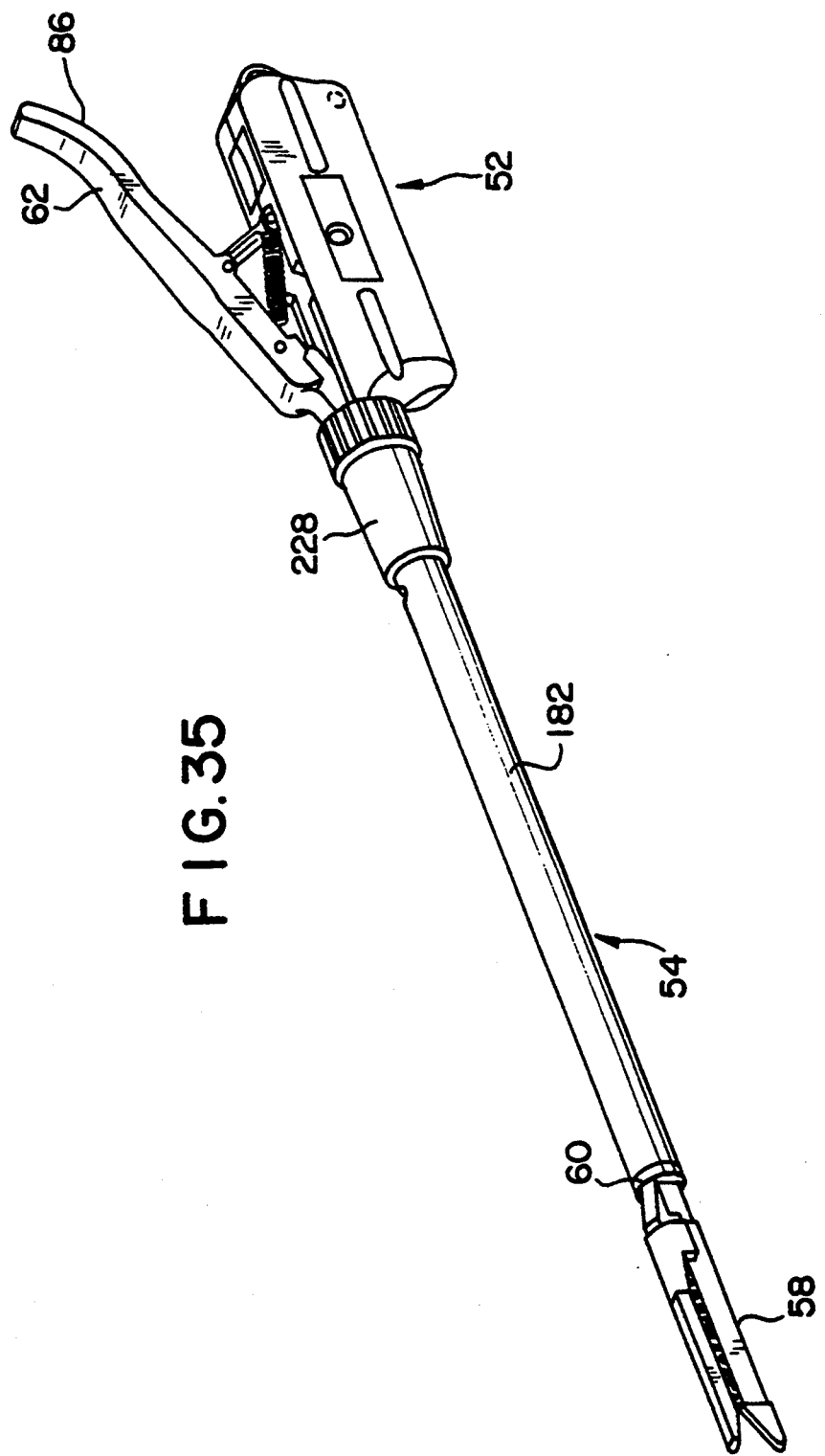
FIG. 35 is a perspective view of another self contained gas powered surgical instrument in accordance with the present invention.
Figure 36:
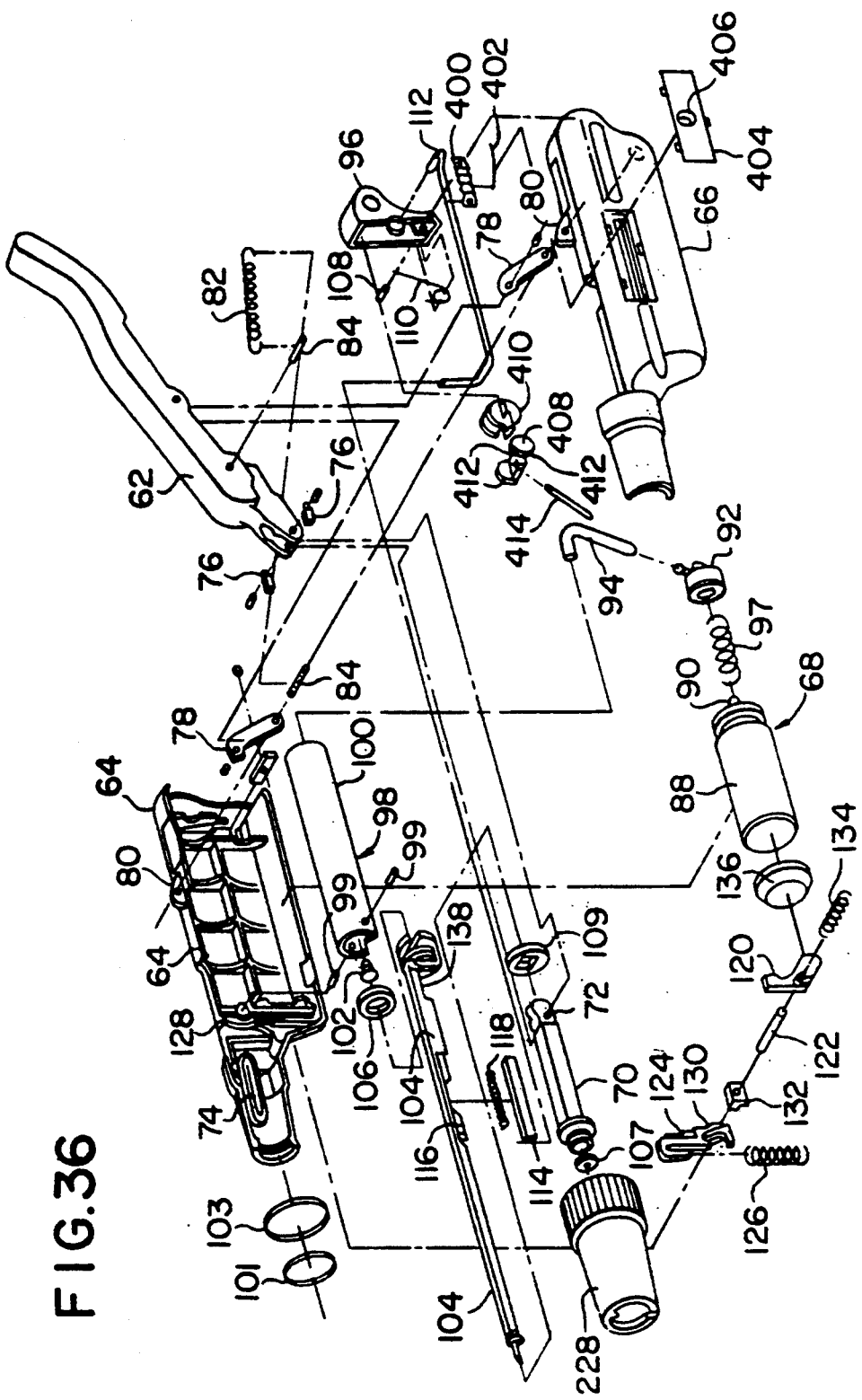
FIG. 36 is an exploded perspective view of the handle portion of the self contained gas powered surgical instrument of FIG. 35.

FIGS. 35–39 show a further embodiment of the present invention similar to that shown in FIGS. 1–15 with the jaw structure of FIGS. 28–34. Referring to Figs. 35–36, the handle portion of this embodiment further includes annular seals 101,103 provided between the distal end of frame 52 and the proximal end of cover tube 182. These seals serve to further inhibit the escape of insufflation gas from the operative site. Seals 107 and 109 are positioned adjacent the proximal and distal ends, respectively, of clamp tube 70 to better seal off insufflation gas from the area of the piston 104.

A counter mechanism is also disposed in handle portion 52 and comprises a counter ratchet 400 attached to trigger rod 112 and a leaf spring 402 mounted in housing 66 so as to engage the teeth on the bottom surface of counter ratchet 400. Numerical indicators are longitudinally disposed on an outer surface of the counter ratchet 400 and correspond to the number of times the instrument has been fired. An access plate 404 having a viewing window 406 therein is positioned in the outside surface of housing 66.

In operation, each time the instrument is fired the leaf spring 402 engages a respective proximally located tooth of the counter ratchet 400, effectively sliding the counter ratchet 400 distally to align the next lower number in viewing window 406. The counter mechanism of this embodiment further includes a locking feature whereby the trigger button 96 is retained in the fired position when the leaf spring 402 engages the most proximal surface of the counter ratchet 400 and prevents the firing rod 112 from returning to its proximal unfired position.

This embodiment of the present invention further includes an integral trigger button rotary safety mechanism comprising a rotary safety shaft 408 disposed within a roller 410. The rotary safety mechanism is rotatably positioned in trigger button 96 with the roller 410 extending out beyond the plane of the back surface of trigger button 96. Projections 412 are eccentrically formed on both sides of rotary safety shaft 408 and extend out beyond the plane of the side surfaces of the trigger button 96. Spring 414 serves to normally bias the rotary safety mechanism with the projections 412 disposed in their distalmost orientation.

Figure 38:
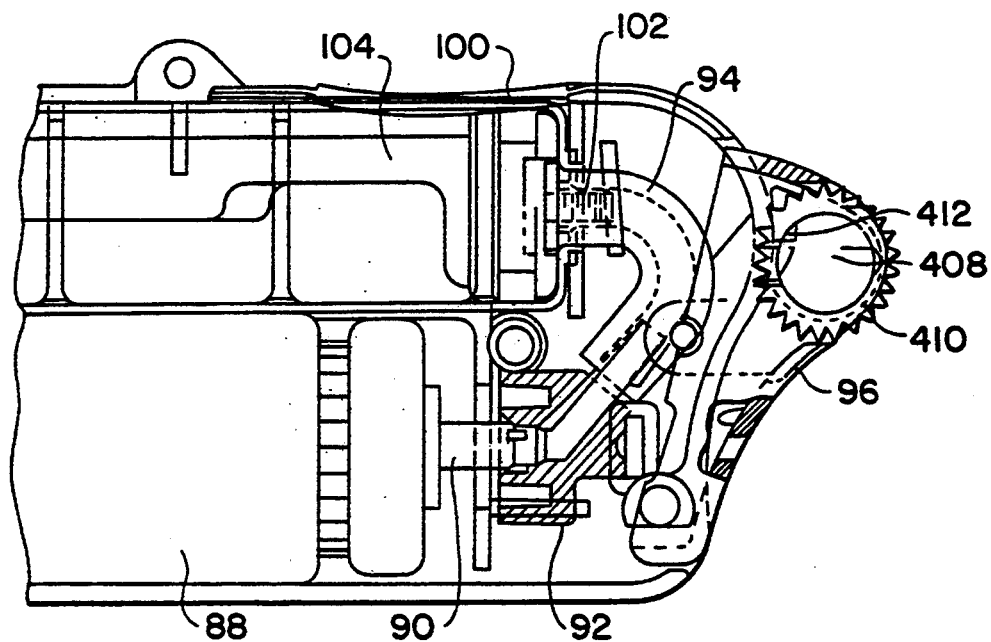
FIGS. 38 and 39 are side cross-sectional views of the firing trigger with integral lockout in the unfired and fired positions.
Figure 39:
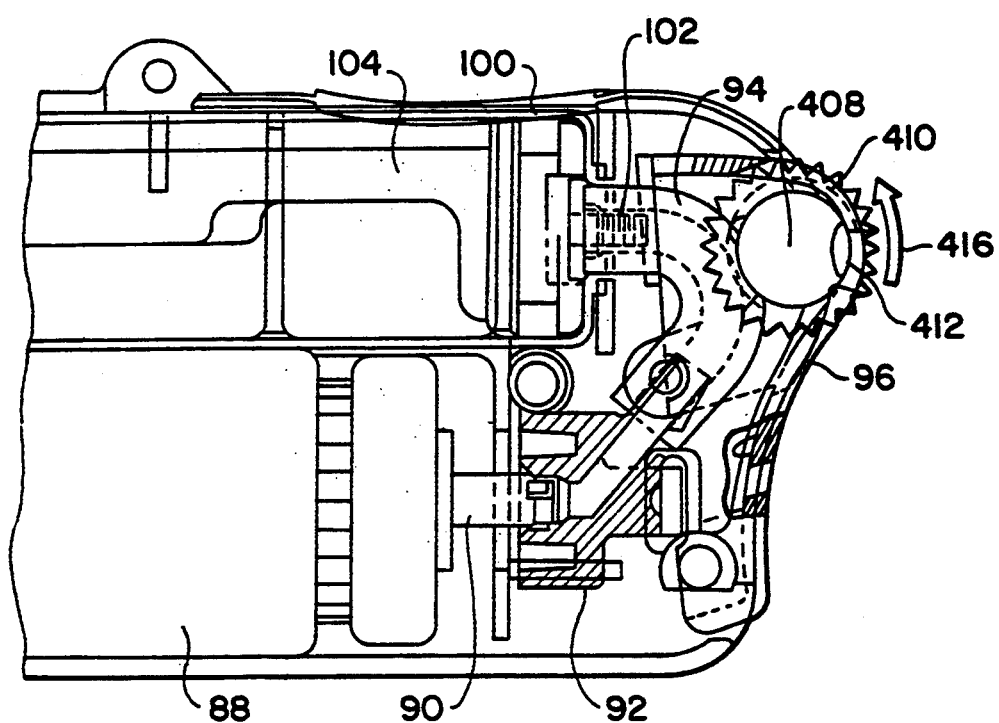

Referring now to FIGS. 38 and 39, in the instrument's unfired position (FIG. 38) projections 412 are in their distalmost position and are disposed in direct alignment with the proximal ends of the housing members 64, 66. In this position, the trigger button 96 cannot be accidentally depressed to fire the instrument. In order to disengage the safety mechanism, the roller 410 is moved in the direction of arrow 416 which serves to rotate projections 412 from their distalmost position (FIG. 38) to their proximalmost position (FIG. 39) effectively allowing trigger button 96 to be depressed to fire the instrument. As soon as roller 410 is released, spring 414 returns the safety mechanism to its normal position to prevent subsequent accidental firings.

FIG. 37 shows the endoscopic portion and the jaw portion of the surgical apparatus of FIG. 35. The anvil 418 of this embodiment is provided with a pair of angled proximal legs 420. This feature permits the anvil 418 to be opened wider to more easily receive tissue between the anvil 418 and cartridge 58. The angled proximal legs 420 preferably extend at an angle of between 0° and 30° from the longitudinal plane of the anvil.

Figure 40:
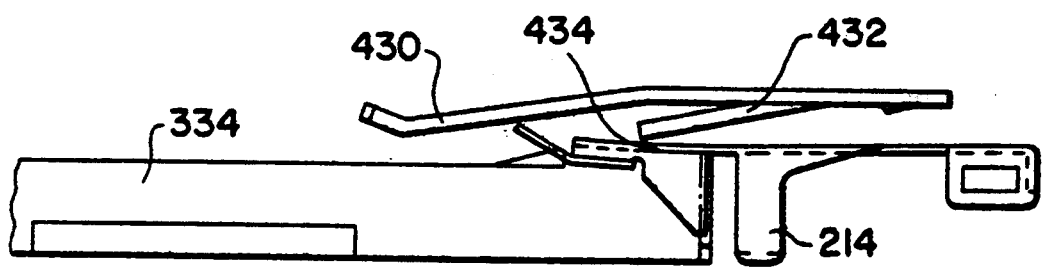
FIGS. 40 and 41 are side views of the cartridge and support structure showing the operation of the clamp lockout structure.
Figure 41:
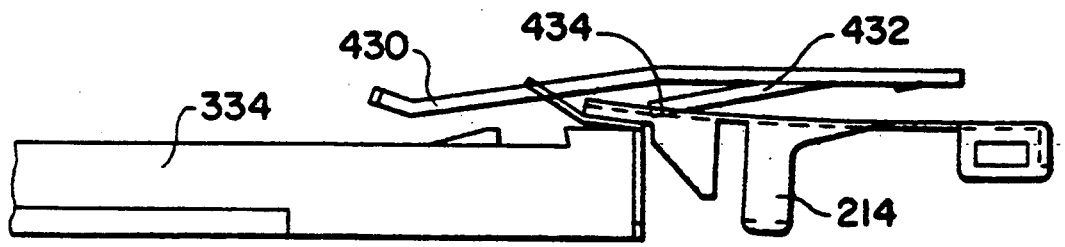

A clamp lockout structure is shown in detail in FIGS. 37, 40 and 41 incorporated into the support structure 214 and upper extension spacer 210. The clamp lockout structure comprises a leaf spring 430 having a diagonally downwardly extending projection 432 attached thereto. A slot 434 is formed through the top surface of support 214 and is adapted to engage and receive projection 432 whenever the support structure is not longitudinally aligned. This clamp lockout structure is designed and configured to prevent the instrument jaws from closing on tissue unless the cartridge and/or jaw elements are properly emplaced within the apparatus.

In operation in the stapling apparatus of FIG. 37, leaf spring 430 and projection 432 are normally disposed above support structure 214. The proximal ends of the cartridge 334 and the anvil 418 are inserted through collar tube 222 and brought into engagement with the distal end of support structure 214. (See FIG. 40) In the event that the cartridge 334 and/or the anvil 418 are not properly and/or completely inserted into engagement with support structure 214, the resulting angular disposition of the support structure 214 brings a slot 434 into alignment with projection 432. (See FIG. 41) As the opera:or attempts It) depress the handle 62, the extension spacer 210 begins to move distally causing projection 432 to enter slot 434 and become entrapped therein effectively preventing any further distal movement of the extension spacer 210 and, in turn, preventing approximation of the anvil 418 and the cartridge 334.

II. Operation of the Instrument

In use, the endoscopic portion of the instrument is inserted into the body, preferably through an endoscopic tube. It is further preferred that the endoscopic tube apparatus be capable of maintaining a sealed pneumoperitoneum, with the internal sealing member of the housing further maintaining this seal despite introduction of the instrument in accordance with the invention into the endoscopic tube. As a practical matter, the jaws of the instrument are closed for insertion into the endoscopic tube, either by pinching the anvil and cartridge prior to insertion or by closing the articulating handle to cam the jaws closed prior to insertion.

After insertion into the endoscopic tube, the endoscopic portion may be rotated in order to appropriately orient the instrument at the stapling site. Rotation of the endoscopic portion relative to the body may be attained by rotating the instrument, as a whole, by rotating the endoscopic portion relative to the frame using rotation knob 228 (See FIG. 1), or by a combination thereof.

Referring to FIGS. 3, 5-8 and 32-34, with the instrument properly oriented so that the tissue to be fastened is disposed between the open jaws of the instrument, i.e., between the tissue contacting surfaces of anvil member 230 and cartridge 302, the jaws are closed to clamp the tissue. In the first embodiment, the surgeon presses down on actuating handle 62, thereby sliding collar tube assembly 220 distally, via clamp tube 70, extension sleeve 204, and extension spacers 210, 2 12.

Figure 32:
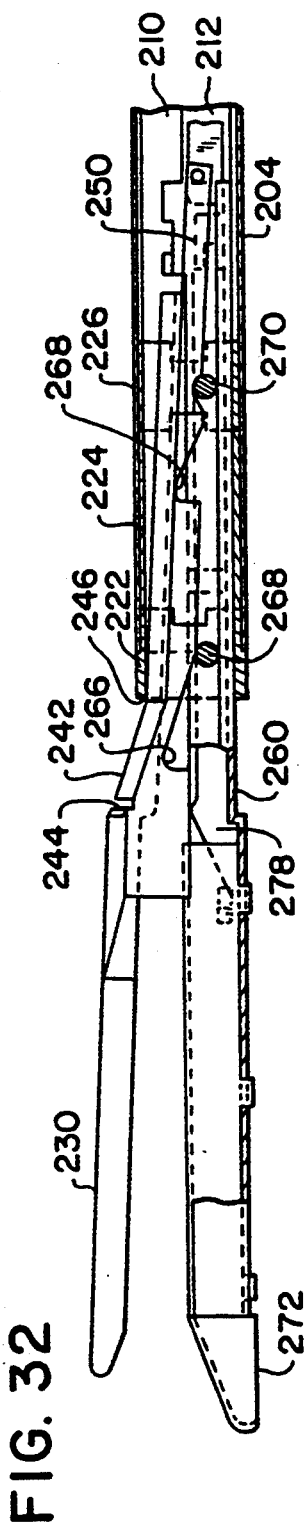
FIGS. 32 through 34 are side plan views in partial cross section of a sequence of operations for the anvil and cartridge assembly of FIG. 30.

Referring to FIGS. 32-34, as collar tube assembly 220 moves distally in the direction of arrow A from a first position where the top arcuate camming surface 246 at the distal end of forward collar tube 222 is proximal to camming surface 242, (FIGS. 32-33), to a second position where the top arcuate camming surface 246 is engaged with locking surface 244, (FIG. 34), the top arcuate camming surface 246 contacts the camming surface of the anvil, thereby forcing the anvil to cam via camming surfaces 264, 266 on camming bosses 268, 270 until the anvil is brought into close cooperative alignment with the cartridge assembly. FIG. 34 illustrates the instrument with the jaws in a closed position.

After closing the instrument jaws, the instrument is ready to be fired. When the surgeon is ready to emplace the staples and cut tissue, firing trigger 96 is depressed to actuate the pneumatic actuator 98 as discussed in detail above. Piston 104, attached to the proximal end of channel 192 is driven distally causing camming surface of forks 194 to ride up and over projection 324 of the cam bar adapter 280 and drive the cam bar adapter in a distal direction. Shear pin 294 is severed and the cam bars and knife are driven longitudinally through the cartridge to sequentially drive and form staples and cut tissue.

As piston 104 contacts return springs 140, 142, pusher washers 186 are compressed on themselves and serve to store energy as the piston moves distally toward the cartridge assembly. This initial compression occurs in the range of between about 20 p.s.i. to about 150 p.s.i. and preferably within a range of about 30 p.s.i. to about 60 p.s.i. Near the end of the distal stroke of the piston 104, this stored energy is released to drive the cam bars 278 through the final distal limits of their travel within the longitudinal slots in the cartridge. At the distal extreme of the longitudinal stroke, the overhanging ledges 306 of cam bars 278 drop over the edge of the cartridge housing thus abutting vertical surface 308 with edge 310.

After firing, return springs 140, 142 engage piston 104 and return it to its original position. The return motion of piston 104 causes rocking lever 120 to be cammed aside by camming surface 144 of piston 104. In the embodiment containing knife 254 discussed above, the cam bars 278 are pulled out of cam bar adapter 280 and remain in position in the longitudinal slots of the cartridge 334. The cam bar adapter, with knife 254 attached, moves proximally within cartridge housing 272 until the outer edges of cam bar adapter 280 impinge on crimps 296.

The cam bar adapter 280 is held in place by crimps 296 while camming surface 200 of fork 194 causes the fork to ride up and disengage with projection 324 of the cam bar adapter. Channel 192 continues to move in the proximal direction until abutting structure 202 is positioned proximally to rearward projection 290 formed in the floor of cartridge housing 260. At this point, the entire cartridge assembly 232 is deactivated.

In the event that the surgeon should accidentally attempt to again fire the instrument without replacing the deactivated cartridge with a new unfired cartridge, the resulting distal longitudinal motion of the channel 192 moves abutting structure 202 into contact with rearward projection 290 effectively preventing further movement of forks 194 toward cam bar adapter 280.

After firing, articulating handle 62 is raised with the assistance of handle return spring 82 which action retracts collar tube assembly 220. This retraction causes anvil 230 to cam out of engagement with cartridge assembly 232. Similarly, raising of articulating handle 62 causes cam slide 124 to move upward disengaging the pneumatic firing mechanism.

In order to replace the cartridge assembly, the instrument is withdrawn from the patient. The cartridge assembly is released and may be removed by pulling it distally out of collar tube assembly 222.

To reinsert a new cartridge assembly, the proximal end of the cartridge assembly is inserted into collar tube assembly 222 until engaging and locking into support structure 214. The instrument is now ready for reinsertion and continued use.

Operation of the instrument with the cartridge and anvil assembly shown in FIGS. 28–31 is substantially similar to that described above. Tubular tissue to be ligated and/or divided is captured within the anvil 352 and the cartridge assembly 330 such that the tissue is transversely oriented therebetween. The cartridge assembly 330 and anvil 352 are approximated by means of camming surfaces 362, 364 and camming bosses 268, 270, as described above. The staples 338 are fired, ligating the tissue.

Unlike the previous embodiment, the cartridge assembly 330 does not include a knife and therefore does not require that the cam bars be retracted by channel 192. In operation, the distal end of channel 192 engages the proximal end of cam bar adapter 350 and drives cam bars 340 to their extreme distal position (FIG. 34). In that position, overhanging ledges 344 drop over the distal end of cartridge housing 332 and remain there. As the piston 104 retracts, channel 192 moves away from cam bar adapter 350 and retracts to a position proximal to rearward project 290, this leaving cam bars 340 and cam bar retainer 350 in the distal position within cartridge assembly 332. Opening, removal and replacement of the deactivated cartridge are effected in substantially the same way as described above with respect to the second alternative embodiment.

It will be understood that various modifications can be made to the various embodiments of the present invention herein disclosed without departing from the spirit and scope thereof. For example, various sizes of the instrument are contemplated, as well as various types of construction materials. Also, various modifications may be made in the configuration of the parts. For example, in the first embodiment the elongated slot for allowing access to the thumbwheel may be placed alternatively in the left body portion or right body portion. Therefore the above description should not be construed as imitating the invention but merely as exemplifications of preferred embodiments thereof. Those skilled in the art will envision other modifications within the scope and spirit of the present invention as defined by the claims appended hereto.

What is claimed is:

1. A sell contained gas powered surgical apparatus for driving surgical fasteners into body tissue comprising:
   a) a frame;
   b) an endoscopic portion defining a longitudinal axis and extending distally from said frame, said endoscopic portion including:
      i) an elongated housing having a distal member for mounting a cartridge assembly, said cartridge assembly including a plurality of surgical fasteners slidably mounted therein, and having a tissue engaging surface;
      ii) an anvil member having a fastener forming surface, said anvil member having a distal end portion and a proximal end portion and being mounted for movement with respect to said elongated housing;
      iii) means for moving said anvil member between an open position spaced from said surgical fasteners and a closed position adjacent said surgical fasteners;
      iv) means for ejecting said surgical fasteners from said cartridge assembly, whereby said fasteners engage said fastener forming surface;
   c) a pneumatic system associated with said frame and adapted to actuate said means for ejecting said surgical fasteners, said pneumatic system including a self contained supply of pressurized gas, a pneumatic actuator mechanism associated with said gas supply, a trigger mechanism mounted for engagement with said pneumatic actuator mechanism to initiate a cycle of firing, a piston and cylinder; and
   d) sequencing means operatively associated with said piston and said supply of pressurized gas for providing a continuous flow of gas to said cylinder sufficient to complete the cycle of firing independent of said trigger mechanism position.

2. The self contained gas powered surgical apparatus as in claim 1 wherein said means for moving said anvil member between said open position and said closed position comprises: a tubular collar disposed around at least a portion of said housing and said anvil, said tubular collar having a distal camming surface and being movable between a first position in which said camming surface is located proximally to the proximal end of said anvil member, and a second position in which said camming surface is located distally to the proximal end portion of said anvil member, said tubular collar cooperating with said anvil member such that when the collar is moved from said first position to said second position, said anvil member is urged to said closed position, and means for moving said collar between said first position and said second position.

3. The self contained gas powered surgical apparatus of claim 1 further comprising means for effectuating rotation of said endoscopic portion about said longitudinal axis thereof.

4. The self contained gas powered surgical apparatus of claim 1 wherein said endoscopic portion is detachably connected to said frame.

5. The self contained gas powered surgical apparatus of claim 1 wherein said anvil member is moved between an open position and a closed position substantially parallel to said tissue engaging surface of said cartridge assembly.

6. The self contained gas powered surgical apparatus of claim 5 further comprising a knife adapted to move with said cam bar.

7. The self contained gas powered surgical apparatus of claim 6 wherein said anvil member is removably mounted to said elongated housing.

8. The self contained gas powered surgical apparatus of claim 1 wherein said means for ejecting said surgical fasteners further comprises pusher elements and at least one cam bar for actuating said pusher elements within said cartridge assembly to drive said surgical fasteners as said cam bar longitudinally traverses said cartridge assembly.

9. The self contained gas powered surgical apparatus of claim 1 wherein said distal member of said elongated housing has a cartridge assembly removably mounted thereto.

10. The self contained gas powered surgical apparatus of claim 1 wherein said pneumatic system further comprises pressure sensing means disposed between said gas supply and said pneumatic actuator mechanism to prevent firing of said surgical apparatus unless a sufficient volume of pressurized gas is available for a complete cycle of firing.

11. The self contained gas powered surgical apparatus of claim 1 further comprising adjusting means for selectively adjusting the longitudinal travel of said means for ejecting said surgical fasteners.

12. The self contained gas powered surgical apparatus of claim 1 wherein said sealing means includes a plurality of sealing members disposed within said endoscopic portion.

13. The self contained gas powered surgical apparatus of claim 1 further comprising locking means for preventing firing of said apparatus after a predetermined number of firings.

14. The self contained gas powered surgical apparatus of claim 1 further comprising counter means for recording the number of times the apparatus has been fired.

15. The self contained gas powered surgical apparatus of claim 14 further comprising display means for displaying indicia providing an indication of the number of times the apparatus has been fired.

16. The self contained gas powered surgical apparatus of claim 1 further comprising safety means for preventing accidental actuation of said pneumatic system.

17. The self contained gas powered surgical apparatus of claim 16 wherein said safety means comprises structure for preventing movement of a trigger adapted to actuate said pneumatic system.

18. The self contained gas powered surgical apparatus of claim 17 wherein said safety means comprises structure pivotally mounted to said trigger and movable between a first position preventing actuation of said pneumatic system and a second position wherein the pneumatic system is actuable.

19. The self contained gas powered surgical apparatus of claim 18 wherein said structure comprises a rotatable wheel normally biased in said first position.

20. The self contained gas powered surgical apparatus of claim 1 wherein said proximal end portion of said anvil member is angled with respect to a longitudinal plane of the anvil member to permit a wider opening of the anvil member in the open position.

21. The self contained gas powered surgical apparatus of claim 20 wherein said proximal end portion of said anvil member is angled between about 0° to 30° from the longitudinal plane of the anvil member.

22. The self contained gas powered surgical apparatus of claim 1 further comprising clamp lockout means for preventing approximation of said anvil and said cartridge when said cartridge or said anvil is not correctly positioned.

23. The self contained gas powered surgical apparatus as in claim 1 wherein said sequencing means comprises a linkage engageable with said pneumatic actuator mechanism.

24. A self contained gas powered endoscopic surgical apparatus for driving surgical fasteners into body tissue comprising:
   a) a frame:
   b) a pneumatic system disposed in said frame including a supply of pressurized gas pneumatically connected to a pneumatic actuator means, said pneumatic actuator means including an actuator, and a piston reciprocally slidable within a cylinder connected to said supply of pressurized gas;
   c) sequencing means operatively associated with said pneumatic system for providing a continuous flow of said pressurized gas to said cylinder sufficient to complete a cycle of firing independent or the position of said actuator;
   d) an endoscopic portion extending distally from said frame, said endoscopic portion including:
      i) an elongated housing having a distal end portion which comprises means to support a plurality of surgical fasteners,
      ii) an anvil member having a fastener forming surface, said anvil member being mounted with respect to said elongated housing such that at least the distal end of said anvil member is movable in directions generally transverse to said longitudinal axis between an open position spaced from said tissue engaging surface and a closed position wherein said fastener forming surface is in close cooperative alignment with said tissue engaging surface,
      iii) means for moving said anvil member between said open position and said closed position, and
      iv) means ejecting said surgical fasteners from said fastener support means; and
   e) linkage means for connecting said pneumatic actuator means to said means for ejecting said surgical fasteners such that said means for ejecting said surgical fasteners is pneumatically driven.

25. A self contained gas powered surgical apparatus as in claim 24 wherein said supply of pressurized gas is replaceable.

26. A self contained gas powered surgical apparatus as in claim 24 wherein said endoscopic portion is rotatable relative to said handle.

27. A self contained gas powered surgical apparatus as in claim 24 further comprising adjustable firing means associated with said pneumatic system for driving said means for ejecting the surgical fasteners through a predetermined longitudinal stroke.

28. A self contained gas powered surgical apparatus as in claim 24 wherein said pneumatic system includes a trigger mechanism and is activatable to move through a complete cycle on a single touch of the trigger mechanism.

29. A self contained gas powered surgical apparatus as in claim 28 further comprising safety means for blocking movement of said trigger mechanism to prevent accidental actuation of said pneumatic system.

30. A self contained gas powered surgical apparatus as in claim 24 further comprising pressure sensing means disposed in line between said gas supply and said pneumatic actuator means to prevent firing of said surgical apparatus unless a sufficient volume of pressurized gas is available for a complete cycle of firing.

31. A self contained gas powered surgical apparatus as in claim 24 wherein said means for ejecting said surgical fasteners further comprises pusher elements and at least one cam bar for actuating said pusher elements within said cartridge assembly to drive said surgical fasteners as said cam bar longitudinally traverses said cartridge assembly.

32. A self contained gas powered surgical apparatus as in claim 31 further comprising a knife adapted to move in cooperation with said cam bar.

33. The self contained gas powered surgical apparatus of claim 24 further comprising locking means for preventing firing of said apparatus after a predetermined number of firings.

34. The self contained gas powered surgical apparatus of claim 33 further comprising display means for displaying indicia providing an indication of the number of times the apparatus has been fired.

35. The self contained gas powered surgical apparatus of claim 24 further comprising counter means for recording the number of times the apparatus has been fired.

36. The self contained gas powered surgical apparatus of claim 45 further comprising clamp lockout means for preventing approximation of said anvil and said cartridge when said cartridge is misaligned with said anvil.

37. A self contained gas powered surgical apparatus for driving surgical fasteners into body tissue comprising:
a) a frame having clamping means and
b) an elongated portion defining a longitudinal axis and extending distally from the frame, said elongated portion including:
  i) an extension tube having a distal end mounted collar tube, the extension tube rotatably connected to the clamping means of the frame for rotatable and longitudinal movement through the elongated portion between a first open position and a second closed position;
  ii) a cover tube mounted to the frame for rotational movement about a longitudinal axis;
  iii) an elongated support fixed to the cover tube, said elongated support retaining a cartridge assembly including plurality of surgical fasteners slidably mounted therein and having a tissue engaging surface and said elongated support retaining an anvil member having a fastener forming surface, the anvil member being movable between an open position corresponding to the first position of the extension tube and a closed position corresponding to the second position of the extension tube wherein the fastener forming surface is in close cooperative alignment with the tissue engaging surface of the cartridge assembly; and
  iv) means for ejecting said surgical fasteners from said cartridge assembly, said means including a channel and a cam bar adapter mounting at least one cam bar for ejecting surgical fasteners, said channel adapted for longitudinal movement within the elongated support and rotational movement with the endoscopic portion,
c) a self contained pneumatic system mounted in said frame and including a supply of low pressure gas and a pneumatic actuator mechanism associated with said gas supply, said pneumatic actuator mechanism including a piston connected to said channel, a cylinder and a firing mechanism mounted to initiate a cycle of firing such that when said firing mechanism is activated, gas from said gas supply passes into said cylinder independent of subsequent positioning of said firing mechanism to drive said piston and channel in a longitudinally distal direction to cause said channel to move said cam bar distally to eject said surgical fasteners through a complete firing cycle after initial actuation;
d) clamp lockout means associated with said clamping means for preventing approximation of said anvil and cartridge unless both are in alignment; and
e) locking means associated with said pneumatic system for preventing firing of said apparatus after a predetermined number of firings.

38. A self contained gas powered surgical apparatus for driving surgical fasteners into body tissue comprising:
a) a frame;
b) an endoscopic portion defining a longitudinal axis and extending distally from said frame, said endoscopic portion including:
  i) an elongated housing having a distal member for mounting a cartridge assembly, said cartridge assembly having a proximal and a distal end portion and including plurality of surgical fasteners slidably mounted therein, and having a tissue engaging surface;
  ii) an anvil member having a fastener forming surface, said anvil member having a distal end portion and a proximal end portion and being mounted with respect to said elongated housing such that at least said distal end portion of said anvil member is movable between an open position spaced from said housing and a closed position wherein said fastener forming surface is in close cooperative alignment with said tissue engaging surface of said cartridge assembly;
  iii) means for moving said anvil member between said open position and said closed position;
  iv) means for sequentially ejecting said surgical fasteners from said cartridge assembly, whereby said fasteners sequentially engage said fastener forming surface; and
c) a pneumatic system disposed in said frame and including a self contained supply of pressurized gas, a pneumatic actuator mechanism associated with said gas supply, and a trigger mechanism mounted for engagement with said actuator mechanism to initiate a firing cycle, said pneumatic system adapted to actuate said means for ejecting said surgical fasteners, said pneumatic system operating said means for sequentially ejecting said surgical fasteners, independent of the position of said trigger mechanism after initial actuation, to complete the firing cycle.

39. In a surgical apparatus for driving surgical fasteners into body tissue, such apparatus having a frame and an elongated portion extending distally from the frame, the elongated portion including a cartridge assembly and a plurality of surgical fasteners slidably mounted therein and an anvil, at least one of the cartridge assembly and the anvil being movable with respect to the other between an open position spaced apart from one another and a closed position adjacent each other the improvement comprising: a self contained pneumatic system mounted to said frame and including a supply of low pressure gas, a pneumatic actuator mechanism associated with said gas supply, and a trigger mechanism mounted for engagement with said pneumatic actuator mechanism to initiate a cycle of firing, said pneumatic actuator mechanism being adapted to cooperate with means for ejecting said surgical fasteners to fire said surgical fasteners against said anvil to complete the cycle of firing independent of the position of said trigger mechanism after initial actuation.

* * * * *